(12) United States Patent
Tran et al.

(10) Patent No.: US 10,704,040 B2
(45) Date of Patent: Jul. 7, 2020

(54) TRIPLE-MODE SYSTEM FOR ANTIBODY MATURATION, SURFACE DISPLAY AND SECRETION

(71) Applicant: Abzyme Therapeutics LLC, Pottstown, PA (US)

(72) Inventors: Hiep Tran, West Chester, PA (US); Xiaole Chen, Exton, PA (US); Hung Pham, Phoenixville, PA (US); Christine Mary Prokopowitz, Douglassville, PA (US); Rolf Swoboda, Upper Darby, PA (US); Ian White, West Chester, PA (US)

(73) Assignee: Abzyme Therapeutics LLC, Pottstown, PA (US)

( * ) Notice: Subject to any disclaimer, the term of this patent is extended or adjusted under 35 U.S.C. 154(b) by 288 days.

(21) Appl. No.: 15/986,025

(22) Filed: May 22, 2018

(65) Prior Publication Data

US 2018/0334668 A1    Nov. 22, 2018

Related U.S. Application Data

(60) Provisional application No. 62/509,360, filed on May 22, 2017.

(51) Int. Cl.
| | |
|---|---|
| *B27L 11/00* | (2006.01) |
| *C12N 15/10* | (2006.01) |
| *C12N 15/81* | (2006.01) |
| *C12Q 1/6897* | (2018.01) |
| *C07K 14/705* | (2006.01) |
| *C12N 9/78* | (2006.01) |
| *C07K 16/00* | (2006.01) |

(52) U.S. Cl.
CPC .... *C12N 15/1055* (2013.01); *C07K 14/70503* (2013.01); *C07K 16/00* (2013.01); *C12N 9/78* (2013.01); *C12N 15/1037* (2013.01); *C12N 15/81* (2013.01); *C12Q 1/6897* (2013.01); *C07K 2317/14* (2013.01); *C07K 2317/56* (2013.01); *C07K 2317/60* (2013.01); *C07K 2318/00* (2013.01); *C07K 2319/02* (2013.01); *C07K 2319/035* (2013.01); *C07K 2319/20* (2013.01); *C07K 2319/70* (2013.01); *C12N 2800/206* (2013.01); *C12N 2800/60* (2013.01); *C12Y 305/04005* (2013.01)

(58) Field of Classification Search
CPC .................................................. C12N 15/1055
See application file for complete search history.

(56) References Cited

U.S. PATENT DOCUMENTS

| | | | | |
|---|---|---|---|---|
| 9,365,846 | B2 * | 6/2016 | Shaheen | C07K 16/00 |
| 9,683,226 | B2 * | 6/2017 | Wang | C07K 16/00 |
| 2018/0334666 | A1 * | 11/2018 | Tran | C07K 16/005 |

OTHER PUBLICATIONS

Shaheen et al. 2013 "A dual-mode surface display system for the maturation and production of monoclonal antibodies in glyco-engineered Pichia pastoris." PLoS One 8: e70190 (Year: 2013).*
Doerner et al. (FEBS Letters 588 (2014) 278-287) (Year: 2014).*
U.S. Appl. No. 16/031,535 is Method for producing semiconductor device.
U.S. Publication No. 2017/0183645 published Jun. 29, 2017 entitled "Composition and Method for Diversifying Polypeptide Libraries".

* cited by examiner

*Primary Examiner* — Scott Long
(74) *Attorney, Agent, or Firm* — Moser Toboada

(57) ABSTRACT

The present invention provides a triple-mode antibody display system that simultaneously matures, displays and secretes an antibody to a target of interest. An antibody in vivo-matured and complexed with membrane anchored bait can be expressed on the surface of the host cell, while complexed with a soluble bait the antibody is secreted from the host cell. Methods of using the system for identifying binders that bind specifically to an antigen of interest are also provided. Polypeptides, polynucleotides and host cells useful for making the protein binder display system are also provided along with methods of use thereof.

21 Claims, 10 Drawing Sheets

Specification includes a Sequence Listing.

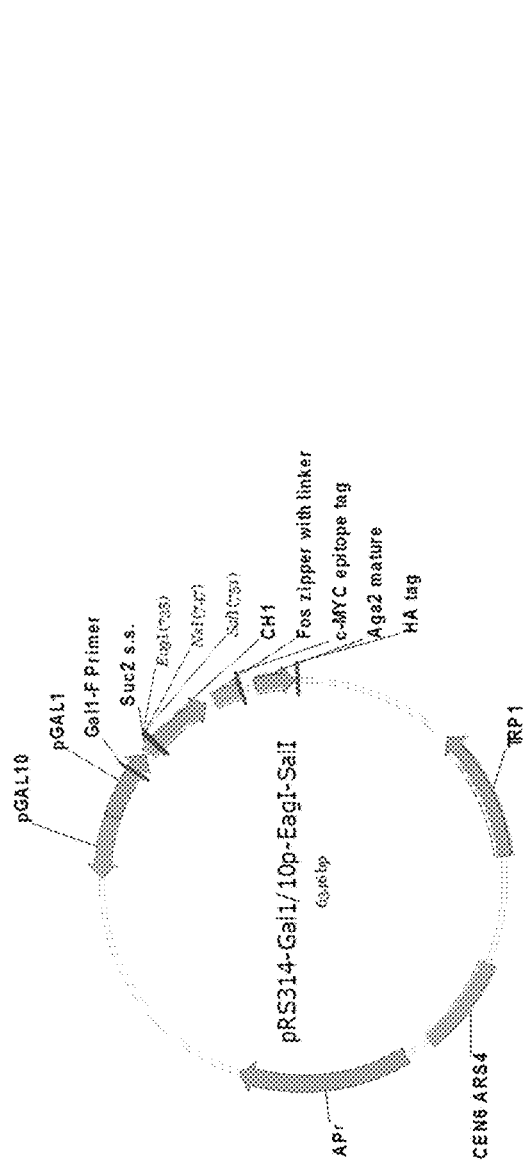
Figure 2C
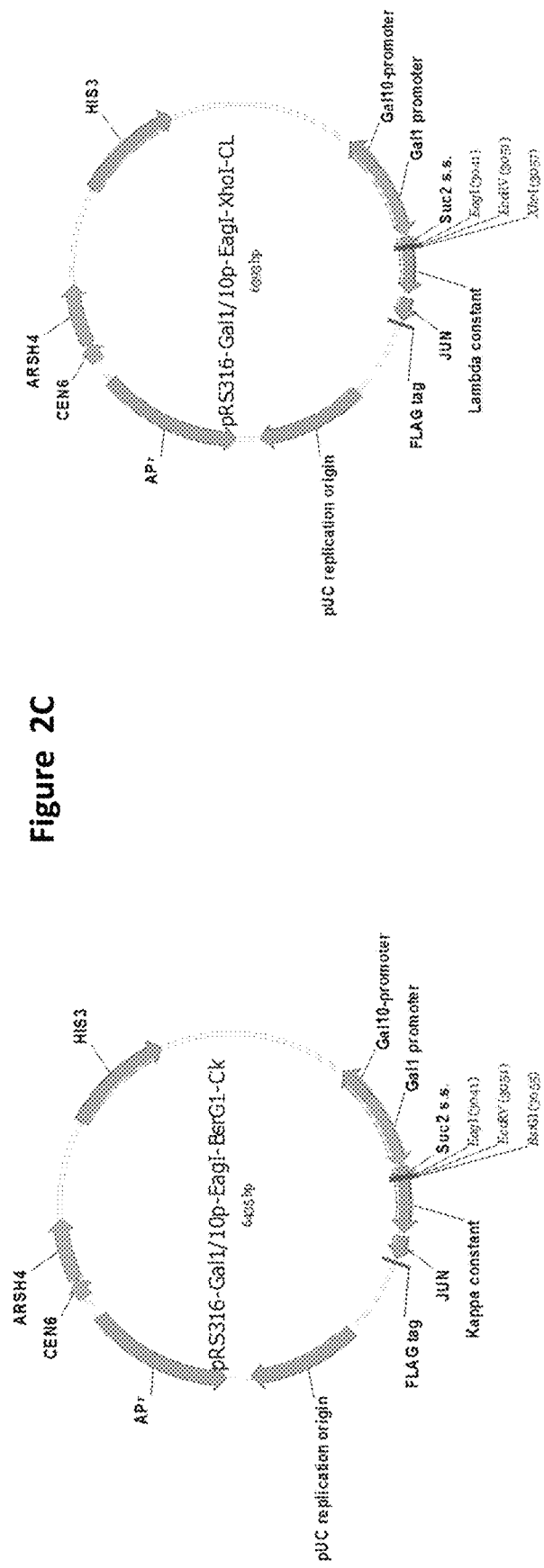
Figure 2E
Figure 2D

SEQUENCE LISTING

```
<160> NUMBER OF SEQ ID NOS: 12

<210> SEQ ID NO 1
<211> LENGTH: 87
<212> TYPE: PRT
<213> ORGANISM: Saccharomyces cerevisiae
```

<400> SEQUENCE: 1

Met Gln Leu Leu Arg Cys Phe Ser Ile Phe Ser Val Ile Ala Ser Val
1               5                   10                  15

Leu Ala Gln Glu Leu Thr Thr Ile Cys Glu Gln Ile Pro Ser Pro Thr
            20                  25                  30

Leu Glu Ser Thr Pro Tyr Ser Leu Ser Thr Thr Thr Ile Leu Ala Asn
        35                  40                  45

Gly Lys Ala Met Gln Gly Val Phe Glu Tyr Tyr Lys Ser Val Thr Phe
50                  55                  60

Val Ser Asn Cys Gly Ser His Pro Ser Thr Thr Ser Lys Gly Ser Pro
65                  70                  75                  80

Ile Asn Thr Gln Tyr Val Phe
                85

<210> SEQ ID NO 2
<211> LENGTH: 725
<212> TYPE: PRT
<213> ORGANISM: Saccharomyces cerevisiae

<400> SEQUENCE: 2

Met Thr Leu Ser Phe Ala His Phe Thr Tyr Leu Phe Thr Ile Leu Leu
1               5                   10                  15

Gly Leu Thr Asn Ile Ala Leu Ala Ser Asp Pro Glu Thr Ile Leu Val
            20                  25                  30

Thr Ile Thr Lys Thr Asn Asp Ala Asn Gly Val Val Thr Thr Thr Val
        35                  40                  45

Ser Pro Ala Leu Val Ser Ser Thr Ile Val Gln Ala Gly Thr Thr
50                  55                  60

Thr Leu Tyr Thr Thr Trp Cys Pro Leu Thr Val Ser Thr Ser Ser Ala
65                  70                  75                  80

Ala Glu Ile Ser Pro Ser Ile Ser Tyr Ala Thr Thr Leu Ser Arg Phe
            85                  90                  95

Ser Thr Leu Thr Leu Ser Thr Glu Val Cys Ser His Glu Ala Cys Pro
            100                 105                 110

Ser Ser Ser Thr Leu Pro Thr Thr Thr Leu Ser Val Thr Ser Lys Phe
            115                 120                 125

Thr Ser Tyr Ile Cys Pro Thr Cys His Thr Thr Ala Ile Ser Ser Leu
        130                 135                 140

Ser Glu Val Gly Thr Thr Val Val Ser Ser Ser Ala Ile Glu Pro
145                 150                 155                 160

Ser Ser Ala Ser Ile Ile Ser Pro Val Thr Ser Thr Leu Ser Ser Thr
                165                 170                 175

Thr Ser Ser Asn Pro Thr Thr Thr Ser Leu Ser Ser Thr Ser Thr Ser
            180                 185                 190

Pro Ser Ser Thr Ser Thr Ser Pro Ser Ser Thr Ser Thr Ser Ser Ser
        195                 200                 205

Ser Thr Ser Thr Ser Ser Ser Thr Ser Ser Ser Ser Ser Ser Ser Thr
210                 215                 220

Ser Thr Ser Pro Ser Ser Thr Ser Thr Ser Ser Ser Leu Thr Ser Thr
225                 230                 235                 240

Ser Ser Ser Ser Thr Ser Thr Ser Gln Ser Ser Thr Ser Thr Ser Ser
                245                 250                 255

Ser Ser Thr Ser Thr Ser Pro Ser Ser Thr Ser Thr Ser Ser Ser Ser
            260                 265                 270

```
Thr Ser Thr Ser Pro Ser Ser Lys Ser Thr Ser Ala Ser Ser Thr Ser
            275                 280                 285

Thr Ser Ser Tyr Ser Thr Ser Thr Ser Pro Ser Leu Thr Ser Ser Ser
            290                 295                 300

Pro Thr Leu Ala Ser Thr Ser Pro Ser Ser Thr Ser Ile Ser Ser Thr
305                     310                 315                 320

Phe Thr Asp Ser Thr Ser Ser Leu Gly Ser Ser Ile Ala Ser Ser Ser
                325                 330                 335

Thr Ser Val Ser Leu Tyr Ser Pro Ser Thr Pro Val Tyr Ser Val Pro
            340                 345                 350

Ser Thr Ser Ser Asn Val Ala Thr Pro Ser Met Thr Ser Ser Thr Val
            355                 360                 365

Glu Thr Thr Val Ser Ser Gln Ser Ser Ser Glu Tyr Ile Thr Lys Ser
            370                 375                 380

Ser Ile Ser Thr Thr Ile Pro Ser Phe Ser Met Ser Thr Tyr Phe Thr
385                     390                 395                 400

Thr Val Ser Gly Val Thr Thr Met Tyr Thr Thr Trp Cys Pro Tyr Ser
                405                 410                 415

Ser Glu Ser Glu Thr Ser Thr Leu Thr Ser Met His Glu Thr Val Thr
            420                 425                 430

Thr Asp Ala Thr Val Cys Thr His Glu Ser Cys Met Pro Ser Gln Thr
            435                 440                 445

Thr Ser Leu Ile Thr Ser Ser Ile Lys Met Ser Thr Lys Asn Val Ala
            450                 455                 460

Thr Ser Val Ser Thr Ser Thr Val Glu Ser Ser Tyr Ala Cys Ser Thr
465                     470                 475                 480

Cys Ala Glu Thr Ser His Ser Tyr Ser Ser Val Gln Thr Ala Ser Ser
                485                 490                 495

Ser Ser Val Thr Gln Gln Thr Thr Ser Thr Lys Ser Trp Val Ser Ser
            500                 505                 510

Met Thr Thr Ser Asp Glu Asp Phe Asn Lys His Ala Thr Gly Lys Tyr
            515                 520                 525

His Val Thr Ser Ser Gly Thr Ser Thr Ile Ser Thr Ser Val Ser Glu
            530                 535                 540

Ala Thr Ser Thr Ser Ser Ile Asp Ser Glu Ser Gln Glu Gln Ser Ser
545                     550                 555                 560

His Leu Leu Ser Thr Ser Val Leu Ser Ser Ser Leu Ser Ala Thr
                565                 570                 575

Leu Ser Ser Asp Ser Thr Ile Leu Leu Phe Ser Ser Val Ser Ser Leu
            580                 585                 590

Ser Val Glu Gln Ser Pro Val Thr Thr Leu Gln Ile Ser Ser Thr Ser
            595                 600                 605

Glu Ile Leu Gln Pro Thr Ser Ser Thr Ala Ile Ala Thr Ile Ser Ala
            610                 615                 620

Ser Thr Ser Ser Leu Ser Ala Thr Ser Ile Ser Thr Pro Ser Thr Ser
625                     630                 635                 640

Val Glu Ser Thr Ile Glu Ser Ser Leu Thr Pro Thr Val Ser Ser
                645                 650                 655

Ile Phe Leu Ser Ser Ser Ser Ala Pro Ser Ser Leu Gln Thr Ser Val
            660                 665                 670

Thr Thr Thr Glu Val Ser Thr Thr Ser Ile Ser Ile Gln Tyr Gln Thr
            675                 680                 685

Ser Ser Met Val Thr Ile Ser Gln Tyr Met Gly Ser Gly Ser Gln Thr
```

```
            690             695             700
Arg Leu Pro Leu Gly Lys Leu Val Phe Ala Ile Met Ala Val Ala Cys
705                 710                 715                 720

Asn Val Ile Phe Ser
            725

<210> SEQ ID NO 3
<211> LENGTH: 208
<212> TYPE: PRT
<213> ORGANISM: Sea Lamprey

<400> SEQUENCE: 3

Met Thr Asp Ala Glu Tyr Val Arg Ile His Glu Lys Leu Asp Ile Tyr
1               5                   10                  15

Thr Phe Lys Lys Gln Phe Phe Asn Asn Lys Lys Ser Val Ser His Arg
            20                  25                  30

Cys Tyr Val Leu Phe Glu Leu Lys Arg Gly Glu Arg Arg Ala Cys
        35                  40                  45

Phe Trp Gly Tyr Ala Val Asn Lys Pro Gln Ser Gly Thr Glu Arg Gly
50                  55                  60

Ile His Ala Glu Ile Phe Ser Ile Arg Lys Val Glu Glu Tyr Leu Arg
65                  70                  75                  80

Asp Asn Pro Gly Gln Phe Thr Ile Asn Trp Tyr Ser Ser Trp Ser Pro
            85                  90                  95

Cys Ala Asp Cys Ala Glu Lys Ile Leu Glu Trp Tyr Asn Gln Glu Leu
            100                 105                 110

Arg Gly Asn Gly His Thr Leu Lys Ile Trp Ala Cys Lys Leu Tyr Tyr
            115                 120                 125

Glu Lys Asn Ala Arg Asn Gln Ile Gly Leu Trp Asn Leu Arg Asp Asn
            130                 135                 140

Gly Val Gly Leu Asn Val Met Val Ser Glu His Tyr Gln Cys Cys Arg
145                 150                 155                 160

Lys Ile Phe Ile Gln Ser Ser His Asn Gln Leu Asn Glu Asn Arg Trp
                165                 170                 175

Leu Glu Lys Thr Leu Lys Arg Ala Glu Lys Arg Ser Glu Leu Ser
            180                 185                 190

Ile Met Ile Gln Val Lys Ile Leu His Thr Thr Lys Ser Pro Ala Val
            195                 200                 205

<210> SEQ ID NO 4
<211> LENGTH: 149
<212> TYPE: PRT
<213> ORGANISM: Saccharomyces cerevisiae

<400> SEQUENCE: 4

Met Thr Leu Ser Phe Ala His Phe Thr Tyr Leu Phe Thr Ile Leu Leu
1               5                   10                  15

Gly Leu Thr Asn Ile Ala Leu Ala Ser Asp Pro Glu Thr Ile Leu Val
            20                  25                  30

Thr Ile Thr Lys Thr Asn Asp Ala Asn Gly Val Val Thr Thr Val
            35                  40                  45

Ser Pro Ala Leu Val Ser Thr Ser Ile Val Gln Ala Gly Thr Thr
        50                  55                  60

Thr Leu Tyr Thr Thr Trp Cys Pro Leu Thr Val Ser Thr Ser Ser Ala
65                  70                  75                  80

Ala Glu Ile Ser Pro Ser Ile Ser Tyr Ala Thr Thr Leu Ser Arg Phe
```

```
                        85                  90                  95
Ser Thr Leu Thr Leu Ser Thr Glu Val Cys Ser His Glu Ala Cys Pro
                100                 105                 110

Ser Ser Ser Thr Leu Pro Thr Thr Leu Ser Val Thr Ser Lys Phe
        115                 120                 125

Thr Ser Tyr Ile Cys Pro Thr Cys His Thr Thr Ala Ile Ser Ser Leu
130                 135                 140

Ser Glu Val Gly Thr
145

<210> SEQ ID NO 5
<211> LENGTH: 331
<212> TYPE: PRT
<213> ORGANISM: Sea Lamprey

<400> SEQUENCE: 5

Met Glu Leu Arg Glu Val Val Asp Cys Ala Leu Ala Ser Cys Val Arg
1               5                   10                  15

His Glu Pro Leu Ser Arg Val Ala Phe Leu Arg Cys Phe Ala Ala Pro
                20                  25                  30

Ser Gln Lys Pro Arg Gly Thr Val Ile Leu Phe Tyr Val Glu Gly Ala
        35                  40                  45

Gly Arg Gly Val Thr Gly Gly His Ala Val Asn Tyr Asn Lys Gln Gly
    50                  55                  60

Thr Ser Ile His Ala Glu Val Leu Leu Ser Ala Val Arg Ala Ala
65                  70                  75                  80

Leu Leu Arg Arg Arg Cys Glu Asp Gly Glu Ala Thr Arg Gly
                85                  90                  95

Cys Thr Leu His Cys Tyr Ser Thr Tyr Ser Pro Cys Arg Asp Cys Val
                100                 105                 110

Glu Tyr Ile Gln Glu Phe Gly Ala Ser Thr Gly Val Arg Val Val Ile
        115                 120                 125

His Cys Cys Arg Leu Tyr Glu Leu Asp Val Asn Arg Arg Ser Glu
    130                 135                 140

Ala Glu Gly Val Leu Arg Ser Leu Ser Arg Leu Gly Arg Asp Phe Arg
145                 150                 155                 160

Leu Met Gly Pro Arg Asp Ala Ile Ala Leu Leu Leu Gly Gly Arg Leu
                165                 170                 175

Ala Asn Thr Ala Asp Gly Glu Ser Gly Ala Ser Gly Asn Ala Trp Val
        180                 185                 190

Thr Glu Thr Asn Val Val Glu Pro Leu Val Asp Met Thr Gly Phe Gly
    195                 200                 205

Asp Glu Asp Leu His Ala Gln Val Gln Arg Asn Lys Gln Ile Arg Glu
210                 215                 220

Ala Tyr Ala Asn Tyr Ala Ser Ala Val Ser Leu Met Leu Gly Glu Leu
225                 230                 235                 240

His Val Asp Pro Asp Lys Phe Pro Phe Leu Ala Glu Phe Leu Ala Gln
                245                 250                 255

Thr Ser Val Glu Pro Ser Gly Thr Pro Arg Glu Thr Arg Gly Arg Pro
        260                 265                 270

Arg Gly Ala Ser Ser Arg Gly Pro Glu Ile Gly Arg Gln Arg Pro Ala
    275                 280                 285

Asp Phe Glu Arg Ala Leu Gly Ala Tyr Gly Leu Phe Leu His Pro Arg
        290                 295                 300
```

-continued

Ile Val Ser Arg Glu Ala Asp Arg Glu Glu Ile Lys Arg Asp Leu Ile
305                 310                 315                 320

Val Val Met Arg Lys His Asn Tyr Gln Gly Pro
                325                 330

<210> SEQ ID NO 6
<211> LENGTH: 269
<212> TYPE: PRT
<213> ORGANISM: Artificial
<220> FEATURE:
<223> OTHER INFORMATION: Camelid VHH chimera with yeast AGA2 anchor

<400> SEQUENCE: 6

Met Leu Leu Gln Ala Phe Leu Phe Leu Leu Ala Gly Phe Ala Ala Lys
1               5                   10                  15

Ile Ser Ala Met Gly Ala Glu Val Gln Leu Val Glu Ser Gly Gly Gly
            20                  25                  30

Leu Val Lys Pro Gly Gly Ser Leu Arg Leu Ser Cys Ser Ala Ser Gly
        35                  40                  45

Phe Thr Phe Asn Ile Tyr Ala Met Asn Trp Val Arg Gln Val Pro Gly
    50                  55                  60

Lys Gly Leu Asp Trp Val Ser Ser Ile Ser Ser Arg Gly Asp Tyr Ile
65                  70                  75                  80

Tyr Tyr Ala Glu Ser Val Glu Gly Arg Phe Thr Ile Ser Arg Asp Asn
                85                  90                  95

Ala Lys Asn Ser Leu Tyr Leu Glu Met Asn Ser Leu Arg Ala Glu Asp
            100                 105                 110

Thr Ala Val Tyr Tyr Cys Ala Arg Ala Gly Leu Gly Thr Val Asp Leu
        115                 120                 125

Arg Trp Gly Gly Ala Phe Asp His Trp Gly Lys Gly Ile Leu Val Thr
    130                 135                 140

Val Ser Ser Ala Ser Gly Leu Lys Gly Pro Arg Asp Asn Arg Val Ile
145                 150                 155                 160

Ala Ser Gly Gly Ser Gly Gly His His His His His His Ala Glu
                165                 170                 175

Asn Leu Tyr Phe Gln Gly Gly Ser Gly Gly Ala Gly Gln Glu Leu
            180                 185                 190

Thr Thr Ile Cys Glu Gln Ile Pro Ser Pro Thr Leu Glu Ser Thr Pro
        195                 200                 205

Tyr Ser Leu Ser Thr Thr Thr Ile Leu Ala Asn Gly Lys Ala Met Gln
    210                 215                 220

Gly Val Phe Glu Tyr Tyr Lys Ser Val Thr Phe Val Ser Asn Cys Gly
225                 230                 235                 240

Ser His Pro Ser Thr Thr Ser Lys Gly Ser Pro Ile Asn Thr Gln Tyr
                245                 250                 255

Val Phe Gly Gly Gly Asp Tyr Lys Asp Asp Asp Asp Lys
            260                 265

<210> SEQ ID NO 7
<211> LENGTH: 392
<212> TYPE: PRT
<213> ORGANISM: Artificial
<220> FEATURE:
<223> OTHER INFORMATION: Yeast AGA1 N-terminal Fragment and yeast CWP1
      Chimera

<400> SEQUENCE: 7

Met Thr Leu Ser Phe Ala His Phe Thr Tyr Leu Phe Thr Ile Leu Leu

```
  1               5                  10                 15
Gly Leu Thr Asn Ile Ala Leu Ala Ser Asp Pro Glu Thr Ile Leu Val
              20                 25                 30

Thr Ile Thr Lys Thr Asn Asp Ala Asn Gly Val Val Thr Thr Thr Val
              35                 40                 45

Ser Pro Ala Leu Val Ser Ser Thr Ile Val Gln Ala Gly Thr Thr
 50                 55                 60

Thr Leu Tyr Thr Thr Trp Cys Pro Leu Thr Val Ser Thr Ser Ser Ala
 65                 70                 75                 80

Ala Glu Ile Ser Pro Ser Ile Ser Tyr Ala Thr Thr Leu Ser Arg Phe
                 85                 90                 95

Ser Thr Leu Thr Leu Ser Thr Glu Val Cys Ser His Glu Ala Cys Pro
             100                105                110

Ser Ser Ser Thr Leu Pro Thr Thr Thr Leu Ser Val Thr Ser Lys Phe
             115                120                125

Thr Ser Tyr Ile Cys Pro Thr Cys His Thr Thr Ala Ile Ser Ser Leu
             130                135                140

Ser Glu Val Gly Thr Gly Gly Gly Lys Pro Ile Pro Asn Pro Leu
145                150                155                160

Leu Gly Leu Asp Ser Thr Gly Gly Ser Gly Gly Asp Ser Glu Glu
             165                170                175

Phe Gly Leu Val Ser Ile Arg Ser Gly Ser Asp Leu Gln Tyr Leu Ser
             180                185                190

Val Tyr Ser Asp Asn Gly Thr Leu Lys Leu Gly Ser Gly Ser
             195                200                205

Phe Glu Ala Thr Ile Thr Asp Asp Gly Lys Leu Lys Phe Asp Asp Asp
210                215                220

Lys Tyr Ala Val Val Asn Glu Asp Gly Ser Phe Lys Glu Gly Ser Glu
225                230                235                240

Ser Asp Ala Ala Thr Gly Phe Ser Ile Lys Asp Gly His Leu Asn Tyr
             245                250                255

Lys Ser Ser Ser Gly Phe Tyr Ala Ile Lys Asp Gly Tyr Ser Ser Tyr
             260                265                270

Ile Phe Ser Ser Lys Gln Ser Asp Asp Ala Thr Gly Val Ala Ile Arg
             275                280                285

Pro Thr Ser Lys Ser Gly Ser Val Ala Ala Asp Phe Ser Pro Ser Asp
             290                295                300

Ser Ser Ser Ser Ser Ser Ala Ser Ala Ser Ala Ser Ala Ser Ser
305                310                315                320

Ser Thr Lys His Ser Ser Ile Glu Ser Val Glu Thr Ser Thr Thr
             325                330                335

Val Glu Thr Ser Ser Ala Ser Ser Pro Thr Ala Ser Val Ile Ser Gln
             340                345                350

Ile Thr Asp Gly Gln Ile Gln Ala Pro Asn Thr Val Tyr Glu Gln Thr
             355                360                365

Glu Asn Ala Gly Ala Lys Ala Ala Val Gly Met Gly Ala Gly Ala Leu
             370                375                380

Ala Val Ala Ala Ala Tyr Leu Leu
385                 390

<210> SEQ ID NO 8
<211> LENGTH: 6236
<212> TYPE: DNA
<213> ORGANISM: Artificial
```

<220> FEATURE:
<223> OTHER INFORMATION: Yeast Expression Vector

<400> SEQUENCE: 8

```
gaattttcaa aaattcttac ttttttttg gatggacgca agaagtttaa ataatcatat      60
tacatggcat taccaccata tacatatcca tatacatatc catatctaat cttacttata    120
tgttgtggaa atgtaaagag ccccattatc ttagcctaaa aaaaccttct ctttggaact    180
ttcagtaata cgcttaactg ctcattgcta tattgaagta cggattagaa gccgccgagc    240
gggtgacagc cctccgaagg aagactctcc tccgtgcgtc ctcgtcttca ccggtcgcgt    300
tcctgaaacg cagatgtgcc tcgcgccgca ctgctccgaa caataaagat tctacaatac    360
tagcttttat ggttatgaag aggaaaaatt ggcagtaacc tggccccaca aaccttcaaa    420
tgaacgaatc aaattaacaa ccataggatg ataatgcgat tagttttta gccttatttc     480
tggggtaatt aatcagcgaa gcgatgattt ttgatctatt aacagatata taaatgcaaa    540
aactgcataa ccactttaac taatactttc aacattttcg gtttgtatta cttcttattc    600
aaatgtaata aaagtatcaa caaaaaattg ttaatatacc tctatacttt aacgtcaagg    660
agaaaaaacc ccggatccat gcttttgcaa gcattccttt tcctttggc tggttttgca     720
gccaaaatat cggccatggg ggccgaagtt cagttggtgg aatctggtgg aggtctggtt    780
aagcctggtg gctcactgag attgtcctgt tcagcctctg gattcacctt caatatctat    840
gccatgaact gggtcagaca ggttccagga aagggtctgg attgggtttc atccattagt    900
agtaggggtg attacatata ctacgcagag tcagtggagg gcagattcac catctccaga    960
gacaacgcca agaactcact gtatctggaa atgaacagcc tgagagccga ggacactgct   1020
gtgtattact gtgctagagc tggtctgggt acagtggatt taaggtgggg tggagccttc   1080
gaccattggg gcaagggaat cctggtcacc gtctcctcag cttctggcct gaaaggccct   1140
agggataaca gggtaattgc ttctggtgga tccggaggtg gtcatcatca ccatcaccat   1200
gctgaaaatt tgtattttca aggtggaggt tccggaggcg ccggtcagga actgacaact   1260
atatgtgagc aaatcccatc accaacttta gaatcgacgc cttactcttt gtcaacgact   1320
actattttgg ccaacggtaa ggcaatgcaa ggagttttg aatattacaa atcagtaacg    1380
tttgtcagta attgtggttc tcatccttca acaactagca aaggctctcc tataaacaca   1440
cagtatgttt ttgagggtgg agattacaag gacgacgatg acaagggtta attaaactag   1500
tgagctccaa ttcgccctat agtgagtcgt attacaattc actggccgtc gttttacaac   1560
gtcgtgactg ggaaaaccct ggcgttaccc aacttaatcg ccttgcagca catcccccct   1620
tcgccagctg gcgtaatagc gaagaggccc gcaccgatcg cccttcccaa cagttgcgca   1680
gcctgaatgg cgaatggcgc gacgcgccct gtagcggcgc attaagcgcg gcgggtgtgg   1740
tggttacgcg cagcgtgacc gctacacttg ccagcgccct agcgcccgct cctttcgctt   1800
tcttcccttc ctttctcgcc acgttcgccg gctttcccg tcaagctcta aatcgggggc    1860
tccctttagg gttccgattt agtgctttac ggcacctcga ccccaaaaaa cttgattagg   1920
gtgatggttc acgtagtggg ccatcgccct gatagacggt ttttcgccct ttgacgttgg   1980
agtccacgtt ctttaatagt ggactcttgt tccaaactgg aacaacactc aaccctatct   2040
cggtctattc ttttgattta agggattt tgccgatttc ggcctattgg ttaaaaaatg     2100
agctgattta acaaaaattt aacgcgaatt ttaacaaaat attaacgttt acaatttcct   2160
gatgcggtat tttctcctta cgcatctgtg cggtatttca caccgcaggc aagtgcacaa   2220
```

```
acaatactta aataaatact actcagtaat aacctatttc ttagcatttt tgacgaaatt    2280 tgctatttg ttagagtctt ttacaccatt tgtctccaca cctccgctta catcaacacc     2340
aataacgcca tttaatctaa gcgcatcacc aacattttct ggcgtcagtc caccagctaa    2400
cataaaatgt aagctttcgg ggctctcttg ccttccaacc cagtcagaaa tcgagttcca    2460
atccaaaagt tcacctgtcc cacctgcttc tgaatcaaac aagggaataa acgaatgagg    2520
tttctgtgaa gctgcactga gtagtatgtt gcagtctttt ggaaatacga gtcttttaat    2580
aactggcaaa ccgaggaact cttggtattc ttgccacgac tcatctccat gcagttggac    2640
gatatcaatg ccgtaatcat tgaccagagc caaaacatcc tccttaggtt gattacgaaa    2700
cacgccaacc aagtatttcg gagtgcctga actatttta tatgctttta caagacttga     2760
aattttcctt gcaataaccg ggtcaattgt tctctttcta ttgggcacac atataatacc    2820
cagcaagtca gcatcggaat ctagagcaca ttctgcggcc tctgtgctct gcaagccgca    2880
aactttcacc aatggaccag aactaccgt gaaattaata acagacatac tccaagctgc     2940
ctttgtgtgc ttaatcacgt atactcacgt gctcaatagt caccaatgcc ctccctcttg    3000
gccctctcct tttcttttt cgaccgaatt aattcttaat cggcaaaaaa agaaaagctc     3060
cggatcaaga ttgtacgtaa ggtgacagc tattttcaa taagaatat cttccactac       3120 tgccatctgg cgtcataact gcaaagtaca catatattac gatgctgtct attaaatgct    3180
tcctatatta tatatatagt aatgtcgttt atggtgcact ctcagtacaa tctgctctga    3240
tgccgcatag ttaagccagc cccgacaccc gccaacaccc gctgacgcgc cctgacgggc    3300
ttgtctgctc ccggcatccg cttacagaca agctgtgacc gtctccggga gctgcatgtg    3360
tcagaggttt tcaccgtcat caccgaaacg cgcgagacga aagggcctcg tgatacgcct    3420 attttatag gttaatgtca tgataataat ggtttcttag gacggatcgc ttgcctgtaa     3480
cttacacgcg cctcgtatct tttaatgatg gaataatttg ggaatttact ctgtgtttat    3540
ttatttttat gttttgtatt tggattttag aaagtaaata aagaaggtag aagagttacg    3600
gaatgaagaa aaaaaaataa acaaaggttt aaaaaatttc aacaaaaagc gtactttaca    3660
tatatattta ttagacaaga aaagcagatt aaatagatat acattcgatt aacgataagt    3720
aaaatgtaaa atcacaggat tttcgtgtgt ggtcttctac acagacaaga tgaaacaatt    3780
cggcattaat acctgagagc aggaagagca agataaaagg tagtatttgt tggcgatccc    3840
cctagagtct tttacatctt cggaaaacaa aaactatttt ttctttaatt tcttttttta    3900 ctttctatt ttaatttata tatttatatt aaaaaatta aattataatt attttatag        3960 cacgtgatga aaaggaccca ggtggcactt tcggggaaa tgtgcgcgga accctatttt     4020 gtttatttt ctaaatacat tcaaatatgt atccgctcat gagacaataa ccctgataaa     4080
tgcttcaata atattgaaaa aggaagagta tgagtattca acatttccgt gtcgccctta    4140
ttcccttttt tgcggcattt tgccttcctg ttttgctca cccagaaacg ctggtgaaag     4200
taaaagatgc tgaagatcag ttgggtgcac gagtgggtta catcgaactg gatctcaaca    4260
gcggtaagat ccttgagagt tttcgccccg aagaacgttt tccaatgatg agcacttta     4320 aagttctgct atgtggcgcg gtattatccc gtattgacgc cgggcaagag caactcggtc    4380
gccgcataca ctattctcag aatgacttgg ttgagtactc accagtcaca gaaaagcatc    4440
ttacggatgg catgacagta agagaattat gcagtgctgc cataaccatg agtgataaca    4500
ctgcggccaa cttacttctg acaacgatcg gaggaccgaa ggagctaacc gcttttttc     4560 acaacatggg ggatcatgta actcgccttg atcgttggga accggagctg aatgaagcca    4620
```

```
taccaaacga cgagcgtgac accacgatgc ctgtagcaat ggcaacaacg ttgcgcaaac    4680
tattaactgg cgaactactt actctagctt cccggcaaca attaatagac tggatggagg    4740
cggataaagt tgcaggacca cttctgcgct cggcccttcc ggctggctgg tttattgctg    4800
ataaatctgg agccggtgag cgtgggtctc gcggtatcat tgcagcactg gggccagatg    4860
gtaagccctc ccgtatcgta gttatctaca cgacgggcag tcaggcaact atggatgaac    4920
gaaatagaca gatcgctgag ataggtgcct cactgattaa gcattggtaa ctgtcagacc    4980
aagtttactc atatatactt tagattgatt taaaacttca ttttttaattt aaaaggatct    5040 aggtgaagat ccttttttgat aatctcatga ccaaaatccc ttaacgtgag ttttcgttcc    5100
actgagcgtc agacccccgta gaaaagatca aggatcttc ttgagatcct ttttttctgc    5160
gcgtaatctg ctgcttgcaa acaaaaaaac caccgctacc agcggtggtt tgtttgccgg    5220
atcaagagct accaactctt tttccgaagg taactggctt cagcagagcg cagataccaa    5280
atactgtcct tctagtgtag ccgtagttag gccaccactt caagaactct gtagcaccgc    5340
ctacatacct cgctctgcta atcctgttac cagtggctgc tgccagtggc gataagtcgt    5400
gtcttaccgg gttggactca agacgatagt taccggataa ggcgcagcgg tcgggctgaa    5460
cggggggttc gtgcacacag cccagcttgg agcgaacgac ctacaccgaa ctgagatacc    5520
tacagcgtga gcattgagaa agcgccacgc ttcccgaagg agaaaggcg gacaggtatc    5580 cggtaagcgg cagggtcgga acaggagagc gcacgaggga gcttccaggg ggaacgcct    5640 ggtatcttta tagtcctgtc gggtttcgcc acctctgact tgagcgtcga ttttttgtgat    5700 gctcgtcagg ggggccgagc ctatggaaaa acgccagcaa cgcggccttt ttacggttcc    5760
tggccttttg ctggcctttt gctcacatgt tctttcctgc gttatcccct gattctgtgg    5820
ataaccgtat taccgccttt gagtgagctg ataccgctcg ccgcagccga acgaccgagc    5880
gcagcgagtc agtgagcgag gaagcggaag agcgcccaat acgcaaaccg cctctccccg    5940
cgcgttggcc gattcattaa tgcagctggc acgacaggtt cccgactgg aaagcgggca    6000 gtgagcgcaa cgcaattaat gtgagttacc tcactcatta ggcacccag gctttacact    6060 ttatgcttcc ggctcctatg ttgtgtggaa ttgtgagcgg ataacaattt cacacaggaa    6120
acagctatga ccatgattac gccaagctcg gaattaaccc tcactaaagg gaacaaaagc    6180
tgggtaccgg gccccccctc gaggtcgacg gtatcgataa gcttgatatc gaattc       6236
```

<210> SEQ ID NO 9
<211> LENGTH: 5815
<212> TYPE: DNA
<213> ORGANISM: Artificial
<220> FEATURE:
<223> OTHER INFORMATION: Yeast Expression Vector

<400> SEQUENCE: 9

```
gaattttcaa aaattcttac ttttttttg gatggacgca aagaagttta ataatcatat     60
tacatggcat taccaccata tacatatcca tatacatatc catatctaat cttacttata    120
tgttgtggaa atgtaaagag ccccattatc ttagcctaaa aaaaccttct ctttggaact    180
ttcagtaata cgcttaactg ctcattgcta tattgaagta cggattagaa gccgccgagc    240
gggtgacagc cctccgaagg aagactctcc tccgtgcgtc ctcgtcttca ccggtcgcgt    300
tcctgaaacg cagatgtgcc tcgcgccgca ctgctccgaa caataaagat tctacaatac    360
tagcttttat ggttatgaag aggaaaaatt ggcagtaacc tggccccaca aaccttcaaa    420
```

```
tgaacgaatc aaattaacaa ccataggatg ataatgcgat tagttttttta gccttatttc    480 tggggtaatt aatcagcgaa gcgatgattt ttgatctatt aacagatata taaatgcaaa    540
aactgcataa ccactttaac taatactttc aacattttcg gtttgtatta cttcttattc    600
aaatgtaata aaagtatcaa caaaaaattg ttaaatatacc tctatacttt aacgtcaagg    660
agaaaaaacc ccggatccac catgcttttg caagcattcc ttttccttttt ggctggtttt    720 gcagccaaaa tatcggccga gatgcattga gcgtcgaccg gtggcggtgg aagcggtgga    780
ggtggctcag gtggtggagg ttcaggaggc gccggtcagg aactgacaac tatatgtgag    840
caaatcccat caccaacttt agaatcgacg ccttactctt tgtcaacgac tactattttg    900
gccaacggta aggcaatgca aggagttttt gaatattaca aatcagtaac gtttgtcagt    960
aattgtggtt ctcatccttc aacaactagc aaaggctctc ctataaacac acagtatgtt   1020
tttggaggtg ataccccata cgatgttcca gattacgctt aaagtgaggt agttaattaa   1080
actagtgagc tccaattcgc cctatagtga gtcgtattac aattcactgg ccgtcgtttt   1140
acaacgtcgt gactgggaaa accctggcgt tacccaactt aatcgccttg cagcacatcc   1200
ccccttcgcc agctggcgta atagcgaaga ggcccgcacc gatcgccctt cccaacagtt   1260
gcgcagcctg aatggcgaat ggcgcgacgc gccctgtagc ggcgcattaa gcgcggcggg   1320
tgtggtggtt acgcgcagcg tgaccgctac acttgccagc gccctagcgc ccgctccttt   1380
cgctttcttc ccttcctttc tcgccacgtt cgccggcttt cccgtcaag ctctaaatcg    1440 ggggctccct ttagggttcc gatttagtgc tttacggcac ctcgacccca aaaaacttga   1500
ttagggtgat ggttcacgta gtgggccatc gccctgatag acggtttttc gccctttgac   1560
gttggagtcc acgttcttta atagtggact cttgttccaa actggaacaa cactcaaccc   1620
tatctcggtc tattctttg atttataagg gattttgccg atttcggcct attggttaaa   1680
aaatgagctg atttaacaaa aatttaacgc gaatttttaac aaaatattaa cgtttacaat   1740
ttcctgatgc ggtatttctc cttacgcat ctgtgcggta tttcacaccg caggcaagtg    1800
cacaaacaat acttaaataa atactactca gtaataacct atttcttagc attttgacg    1860 aaatttgcta ttttgttaga gtcttttaca ccatttgtct ccacacctcc gcttacatca   1920
acaccaataa cgccatttaa tctaagcgca tcaccaacat tttctggcgt cagtccacca   1980
gctaacataa aatgtaagct ttcgggctc tcttgcctc caacccagtc agaaatcgag    2040
ttccaatcca aaagttcacc tgtcccacct gcttctgaat caaacaaggg aataaacgaa   2100
tgaggtttct gtgaagctgc actgagtagt atgttgcagt cttttggaaa tacgagtctt   2160
ttaataactg gcaaaccgag gaactcttgg tattcttgcc acgactcatc tccatgcagt   2220
tggacgatat caatgccgta atcattgacc agagccaaaa catcctcctt aggttgatta   2280
cgaaacacgc caaccaagta tttcggagtg cctgaactat ttttatatgc ttttacaaga   2340
cttgaaattt tccttgcaat aaccgggtca attgttctct ttctattggg cacacatata   2400
atacccagca agtcagcatc ggaatctaga gcacattctg cggcctctgt gctctgcaag   2460
ccgcaaactt tcaccaatgg accagaacta cctgtgaaat taataacaga catactccaa   2520
gctgcctttg tgtgcttaat cacgtatact cacgtgctca atagtcacca atgccctccc   2580
tcttggccct ctcctttct ttttcgacc gaattaattc ttaatcggca aaaaagaaa    2640 agctccggat caagattgta cgtaaggtga caagctattt tcaataaag aatatcttcc    2700 actactgcca tctggcgtca taactgcaaa gtacacatat attacgatgc tgtctattaa   2760
atgcttccta tattatatat atagtaatgt cgtttatggt gcactctcag tacaatctgc   2820
```

```
tctgatgccg catagttaag ccagccccga cacccgccaa cacccgctga cgcgccctga    2880
cgggcttgtc tgctcccggc atccgcttac agacaagctg tgaccgtctc cgggagctgc    2940
atgtgtcaga ggttttcacc gtcatcaccg aaacgcgcga gacgaaaggg cctcgtgata    3000
cgcctatttt tataggttaa tgtcatgata ataatggttt cttaggacgg atcgcttgcc    3060
tgtaacttac acgcgcctcg tatcttttaa tgatggaata atttgggaat ttactctgtg    3120
tttatttatt tttatgtttt gtatttggat tttagaaagt aaataaagaa ggtagaagag    3180
ttacggaatg aagaaaaaaa aataaacaaa ggtttaaaaa atttcaacaa aaagcgtact    3240
ttacatatat atttattaga caagaaaagc agattaaata gatatacatt cgattaacga    3300
taagtaaaat gtaaaatcac aggattttcg tgtgtggtct tctacacaga caagatgaaa    3360
caattcggca ttaatacctg agagcaggaa gagcaagata aaaggtagta tttgttggcg    3420 atcccctag agtcttttac atcttcggaa aacaaaaact attttttctt taatttcttt    3480
ttttactttc tattttaat ttatatattt atattaaaaa atttaaatta taattatttt    3540
tatagcacgt gatgaaaagg acccaggtgg cactttttcgg ggaaatgtgc gcggaacccc    3600
tatttgttta tttttctaaa tacattcaaa tatgtatccg ctcatgagac aataaccctg    3660
ataaatgctt caataatatt gaaaaaggaa gagtatgagt attcaacatt tccgtgtcgc    3720
ccttattccc ttttttgcgg catttttgcct tcctgttttt gctcacccag aaacgctggt    3780
gaaagtaaaa gatgctgaag atcagttggg tgcacgagtg ggttacatcg aactggatct    3840
caacagcggt aagatccttg agagttttcg ccccgaagaa cgttttccaa tgatgagcac    3900
ttttaaagtt ctgctatgtg gcgcggtatt atcccgtatt gacgccgggc aagagcaact    3960
cggtcgccgc atacactatt ctcagaatga cttggttgag tactcaccag tcacagaaaa    4020
gcatcttacg gatggcatga cagtaagaga attatgcagt gctgccataa ccatgagtga    4080
taacactgcg gccaacttac ttctgacaac gatcggagga ccgaaggagc taaccgcttt    4140
ttttcacaac atgggggatc atgtaactcg ccttgatcgt tgggaaccgg agctgaatga    4200
agccatacca aacgacgagc gtgacaccac gatgcctgta gcaatggcaa caacgttgcg    4260
caaactatta actggcgaac tacttactct agcttcccgg caacaattaa tagactggat    4320
ggaggcggat aaagttgcag gaccacttct gcgctcggcc cttccggctg gctggtttat    4380
tgctgataaa tctggagccg gtgagcgtgg gtctcgcggt atcattgcag cactggggcc    4440
agatggtaag ccctcccgta tcgtagttat ctacacgacg ggcagtcagg caactatgga    4500
tgaacgaaat agacagatcg ctgagatagg tgcctcactg attaagcatt ggtaactgtc    4560
agaccaagtt tactcatata ctttagat tgatttaaaa cttcatttt aatttaaaag    4620 gatctaggtg aagatccttt ttgataatct catgaccaaa atcccttaac gtgagttttc    4680
gttccactga gcgtcagacc ccgtagaaaa gatcaaagga tcttcttgag atccttttt    4740 tctgcgcgta atctgctgct tgcaaacaaa aaaaccaccg ctaccagcgg tggtttgttt    4800
gccggatcaa gagctaccaa ctctttttcc gaaggtaact ggcttcagca gagcgcagat    4860
accaaatact gtccttctag tgtagccgta gttaggccac cacttcaaga actctgtagc    4920
accgcctaca tacctcgctc tgctaatcct gttaccagtg gctgctgcca gtggcgataa    4980
gtcgtgtctt accgggttgg actcaagacg atagttaccg gataaggcgc agcggtcggg    5040
ctgaacgggg ggttcgtgca cacagcccag cttggagcga acgacctaca ccgaactgag    5100
atacctacag cgtgagcatt gagaaagcgc cacgcttccc gaagggagaa aggcggacag    5160
```

```
gtatccggta agcggcaggg tcggaacagg agagcgcacg agggagcttc caggggggaa      5220
cgcctggtat ctttatagtc ctgtcgggtt tcgccacctc tgacttgagc gtcgattttt      5280
gtgatgctcg tcagggggc cgagcctatg aaaaacgcc agcaacgcgg cctttttacg       5340
gttcctggcc ttttgctggc cttttgctca catgttcttt cctgcgttat ccctgattc      5400 tgtggataac cgtattaccg cctttgagtg agctgatacc gctcgccgca gccgaacgac      5460
cgagcgcagc gagtcagtga gcgaggaagc ggaagagcgc ccaatacgca aaccgcctct      5520
ccccgcgcgt tggccgattc attaatgcag ctggcacgac aggtttcccg actggaaagc      5580
gggcagtgag cgcaacgcaa ttaatgtgag ttacctcact cattaggcac cccaggcttt      5640
acactttatg cttccggctc ctatgttgtg tggaattgtg agcggataac aatttcacac      5700
aggaaacagc tatgaccatg attacgccaa gctcggaatt aaccctcact aaagggaaca      5760
aaagctgggt accgggcccc ccctcgacgg tatcgataag cttgatatcg aattc          5815

<210> SEQ ID NO 10
<211> LENGTH: 6346
<212> TYPE: DNA
<213> ORGANISM: Artificial
<220> FEATURE:
<223> OTHER INFORMATION: Yeast Expression Vector

<400> SEQUENCE: 10
gaattttcaa aaattcttac ttttttttg gatggacgca aagaagttta ataatcatat         60
tacatggcat taccaccata tacatatcca tatacatatc catatctaat cttacttata       120
tgttgtggaa atgtaaagag ccccattatc ttagcctaaa aaaaccttct ctttggaact       180
ttcagtaata cgcttaactg ctcattgcta tattgaagta cggattagaa gccgccgagc       240
gggtgacagc cctccgaagg aagactctcc tccgtgcgtc ctcgtcttca ccggtcgcgt       300
tcctgaaacg cagatgtgcc tcgcgccgca ctgctccgaa caataaagat tctacaatac       360 tagctttat ggttatgaag aggaaaaatt ggcagtaacc tggccccaca aaccttcaaa       420
tgaacgaatc aaattaacaa ccataggatg ataatgcgat tagtttttta gccttatttc       480
tggggtaatt aatcagcgaa gcgatgattt ttgatctatt aacagatata taatgcaaa       540 aactgcataa ccactttaac taatactttc aacattttcg gtttgtatta cttcttattc       600
aaatgtaata aagtatcaa caaaaaattg ttaatatacc tctatacttt aacgtcaagg       660
agaaaaaacc ccggatccac catgcttttg caagcattcc ttttcctttt ggctggtttt       720
gcagccaaaa tatcggccga gatgcatgcg tcgaccaagg gcccatcggt cttcccctg       780 gcaccctcct ccaagagcac ctctggggc acagcggccc tgggctgcct ggtcaaggac       840
tacttccccg aacctgtgac ggtctcgtgg aactcaggcg ccctgaccag cggcgtgcac       900
accttcccgg ctgtcctaca gtcctcagga ctctactccc tcagcagcgt ggtgaccgtg       960
ccctccagca gcttgggcac ccagacctac atctgcaacg tgaatcacaa gcccagcaac     1020
accaaggtgg acaagaaagt tgagcccaaa tcttgtgaca aaactcacag cccaccgtct     1080
ccagcttctt caagtggtgg actgcagagc ggtggtggag gaggtctgac tgatacactc     1140
caagcggaga cagaccaact agaagatgag aagtctgctt tgcagaccga gattgccaac     1200
ctgctgaagg agaaggaaaa actagagttc atcctggcag ctcacgaatt cctgcaggaa     1260
cagaagttga tttccgaaga agaacctcgga ggtggcatta ccctgttatc cctatcagga     1320
ggcgccggtc aggaactgac aactatatgt gagcaaatcc catcaccaac tttagaatcg     1380
acgccttact ctttgtcaac gactactatt ttggccaacg gtaaggcaat gcaaggagtt     1440
```

```
tttgaatatt acaaatcagt aacgtttgtc agtaattgtg gttctcatcc ttcaacaact      1500
agcaaaggct ctcctataaa cacacagtat gtttttggag gtggataccc atacgatgtt      1560
ccagattacg cttaaattac cctgttatcc ctaagtgagg tagttaatta aactagtgag      1620
ctccaattcg ccctatagtg agtcgtatta caattcactg gccgtcgttt tacaacgtcg      1680
tgactgggaa aaccctggcg ttacccaact aatcgcctt gcagcacatc cccccttcgc       1740
cagctggcgt aatagcgaag aggcccgcac cgatcgccct tcccaacagt tgcgcagcct      1800
gaatggcgaa tggcgcgacg cgccctgtag cggcgcatta agcgcggcgg gtgtggtggt      1860
tacgcgcagc gtgaccgcta cacttgccag cgccctagcg cccgctcctt tcgctttctt      1920
cccttccttt ctcgccacgt tcgccggctt tccccgtcaa gctctaaatc ggggctccc       1980 tttagggttc cgatttagtg ctttacggca cctcgacccc aaaaaacttg attagggtga      2040
tggttcacgt agtgggccat cgccctgata gacggttttt cgccctttga cgttggagtc      2100
cacgttcttt aatagtggac tcttgttcca aactggaaca acactcaacc ctatctcggt      2160
ctattctttt gatttataag ggattttgcc gatttcggcc tattggttaa aaaatgagct      2220
gatttaacaa aaatttaacg cgaattttaa caaaatatta acgtttacaa tttcctgatg      2280
cggtattttc tccttacgca tctgtgcggt atttcacacc gcaggcaagt gcacaaacaa      2340
tacttaaata aatactactc agtaataacc tatttcttag cattttttgac gaaatttgct      2400 attttgttag agtcttttac accatttgtc tccacacctc cgcttacatc aacaccaata      2460
acgccattta atctaagcgc atcaccaaca ttttctggcg tcagtccacc agctaacata      2520
aaatgtaagc tttcggggct ctcttgcctt ccaacccagt cagaaatcga gttccaatcc      2580
aaaagttcac ctgtcccacc tgcttctgaa tcaaacaagg gaataaacga atgaggtttc      2640
tgtgaagctg cactgagtag tatgttgcag tcttttggaa atacgagtct tttaataact      2700
ggcaaaccga ggaactcttg gtattcttgc cacgactcat ctccatgcag ttggacgata      2760
tcaatgccgt aatcattgac cagagccaaa acatcctcct taggttgatt acgaaacacg      2820
ccaaccaagt atttcggagt gcctgaacta tttttatatg cttttacaag acttgaaatt      2880
ttccttgcaa taaccgggtc aattgttctc tttctattgg gcacacatat aatacccagc      2940
aagtcagcat cggaatctag agcacattct gcggcctctg tgctctgcaa gccgcaaact      3000
ttcaccaatg gaccagaact acctgtgaaa ttaataacag acatactcca agctgccttt      3060
gtgtgcttaa tcacgtatac tcacgtgctc aatagtcacc aatgccctcc ctcttggccc      3120
tctccttttc ttttttcgac cgaattaatt cttaatcggc aaaaaaagaa aagctccgga      3180
tcaagattgt acgtaaggtg acaagctatt tttcaataaa gaatatcttc cactactgcc      3240
atctggcgtc ataactgcaa agtacacata tattacgatg ctgtctatta aatgcttcct      3300
atattatata tatagtaatg tcgtttatgg tgcactctca gtacaatctg ctctgatgcc      3360
gcatagttaa gccagccccg acacccgcca cacccgctg acgcgccctg acgggcttgt       3420
ctgctcccgg catccgctta cagacaagct gtgaccgtct ccgggagctg catgtgtcag      3480
aggttttcac cgtcatcacc gaaacgcgcg agacgaaagg gcctcgtgat acgcctattt      3540
ttataggtta atgtcatgat aataatggtt tcttaggacg atcgcttgc ctgtaactta       3600 cacgcgcctc gtatctttta atgatggaat aatttgggaa tttactctgt gtttatttat      3660
ttttatgttt tgtatttgga ttttagaaag taaataaaga aggtagaaga gttacggaat      3720
gaagaaaaaa aaataaacaa aggtttaaaa aatttcaaca aaaagcgtac tttacatata      3780
```

```
tatttattag acaagaaaag cagattaaat agatatacat tcgattaacg ataagtaaaa    3840
tgtaaaatca caggattttc gtgtgtggtc ttctacacag acaagatgaa acaattcggc    3900
attaatacct gagagcagga agagcaagat aaaaggtagt atttgttggc gatcccccta    3960
gagtctttta catcttcgga aaacaaaaac tatttttttct ttaatttctt tttttacttt    4020
ctatttttaa tttatatatt tatattaaaa aatttaaatt ataattattt ttatagcacg    4080
tgatgaaaag gacccaggtg gcacttttcg gggaaatgtg cgcggaaccc ctatttgttt    4140
attttttctaa atacattcaa atatgtatcc gctcatgaga caataaccct gataaatgct    4200
tcaataatat tgaaaaagga agagtatgag tattcaacat ttccgtgtcg cccttattcc    4260
cttttttgcg gcattttgcc ttcctgtttt tgctcaccca gaaacgctgg tgaaagtaaa    4320
agatgctgaa gatcagttgg gtgcacgagt gggttacatc gaactggatc tcaacagcgg    4380
taagatcctt gagagttttc gccccgaaga acgttttcca atgatgagca cttttaaagt    4440
tctgctatgt ggcgcggtat tatcccgtat tgacgccggg caagagcaac tcggtcgccg    4500
catacactat tctcagaatg acttggttga gtactcacca gtcacagaaa agcatcttac    4560
ggatggcatg acagtaagag aattatgcag tgctgccata accatgagtg ataacactgc    4620
ggccaactta cttctgacaa cgatcggagg accgaaggag ctaaccgctt ttttcacaa    4680
catgggggat catgtaactc gccttgatcg ttgggaaccg gagctgaatg aagccatacc    4740
aaacgacgag cgtgacacca cgatgcctgt agcaatggca acaacgttgc gcaaactatt    4800
aactggcgaa ctacttactc tagcttcccg gcaacaatta atagactgga tggaggcgga    4860
taaagttgca ggaccacttc tgcgctcggc ccttccggct ggctggttta ttgctgataa    4920
atctggagcc ggtgagcgtg ggtctcgcgg tatcattgca gcactggggc cagatggtaa    4980
gccctcccgt atcgtagtta tctacacgac gggcagtcag gcaactatgg atgaacgaaa    5040
tagacagatc gctgagatag gtgcctcact gattaagcat tggtaactgt cagaccaagt    5100
ttactcatat atactttaga ttgatttaaa acttcatttt taatttaaaa ggatctaggt    5160
gaagatcctt tttgataatc tcatgaccaa aatcccttaa cgtgagtttt cgttccactg    5220
agcgtcagac cccgtagaaa agatcaaagg atcttcttga gatcctttt ttctgcgcgt    5280
aatctgctgc ttgcaaacaa aaaaaccacc gctaccagcg gtggtttgtt tgccggatca    5340
agagctacca actcttttc cgaaggtaac tggcttcagc agagcgcaga taccaaatac    5400
tgtccttcta gtgtagccgt agttaggcca ccacttcaag aactctgtag caccgcctac    5460
atacctcgct ctgctaatcc tgttaccagt ggctgctgcc agtggcgata agtcgtgtct    5520
taccgggttg gactcaagac gatagttacc ggataaggcg cagcggtcgg gctgaacggg    5580
gggttcgtgc acacagccca gcttggagcg aacgacctac accgaactga gatacctaca    5640
gcgtgagcat tgagaaagcg ccacgcttcc cgaagggaga aaggcggaca ggtatccggt    5700
aagcggcagg gtcggaacag gagagcgcac gagggagctt ccagggggga acgcctggta    5760
tctttatagt cctgtcgggt ttcgccacct ctgacttgag cgtcgatttt tgtgatgctc    5820
gtcagggggg ccgagcctat ggaaaaacgc cagcaacgcg gcctttttac ggttcctggc    5880
cttttgctgg ccttttgctc acatgttctt tcctgcgtta tcccctgatt ctgtggataa    5940
ccgtattacc gcctttgagt gagctgatac cgctcgccgc agccgaacga ccgagcgcag    6000
cgagtcagtg agcgaggaag cggaagagcg cccaatacgc aaaccgcctc tccccgcgcg    6060
ttggccgatt cattaatgca gctggcacga caggtttccc gactggaaag cgggcagtga    6120
gcgcaacgca attaatgtga gttacctcac tcattaggca ccccaggctt tacactttat    6180
```

```
gcttccggct cctatgttgt gtggaattgt gagcggataa caatttcaca caggaaacag    6240
ctatgaccat gattacgcca agctcggaat taaccctcac taaagggaac aaaagctggg    6300
taccgggccc ccctcgacg gtatcgataa gcttgatatc gaattc                   6346
```

<210> SEQ ID NO 11
<211> LENGTH: 6435
<212> TYPE: DNA
<213> ORGANISM: Artificial
<220> FEATURE:
<223> OTHER INFORMATION: Yeast Expression Vector

<400> SEQUENCE: 11

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctgg cttaactatg cggcatcaga gcagattgta ctgagagtgc      180
accataattc cgttttaaga gcttggtgag cgctaggagt cactgccagg tatcgtttga     240
acacggcatt agtcagggaa gtcataacac agtccttcc cgcaatttc ttttctatt        300 actcttggcc tcctctagta cactctatat tttttatgc ctcggtaatg attttcattt      360
ttttttttcc acctagcgga tgactctttt tttttcttag cgattggcat tatcacataa     420
tgaattatac attatataaa gtaatgtgat ttcttcgaag aatatactaa aaaatgagca     480
ggcaagataa acgaaggcaa agatgacaga gcagaaagcc ctagtaaagc gtattacaaa     540
tgaaaccaag attcagattg cgatctcttt aaagggtggt cccctagcga tagagcactc     600
gatcttccca gaaaaagagg cagaagcagt agcagaacag gccacacaat cgcaagtgat     660
taacgtccac acaggtatag ggtttctgga ccatatgata catgtctctgg ccaagcattc    720 cggctggtcg ctaatcgttg agtgcattgg tgacttacac atagacgacc atcacaccac     780
tgaagactgc gggattgctc tcggtcaagc ttttaaagag gccctactgg cgcgtggagt     840
aaaaaggttt ggatcaggat ttgcgccttt ggatgaggca ctttccagag cggtggtaga    900
tctttcgaac aggccgtacg cagttgtcga acttggtttg caaagggaga agtaggaga      960 tctctcttgc gagatgatcc cgcatttct tgaaagcttt gcagaggcta gcagaattac    1020
cctccacgtt gattgtctgc gaggcaagaa tgatcatcac cgtagtgaga gtgcgttcaa    1080
ggctcttgcg gttgccataa gagaagccac ctcgcccaat ggtaccaacg atgttccctc    1140
caccaaaggt gttcttatgt agtgacaccg attatttaaa gctgcagcat acgatatata    1200
tacatgtgta tatatgtata cctatgaatg tcagtaagta tgtatacgaa cagtatgata    1260
ctgaagatga caaggtaatg catcattcta tacgtgtcat tctgaacgag gcgcgctttc    1320
cttttttctt tttgcttttt cttttttttt ctcttgaact cgacggatct atgcggtgtg    1380
aaataccgca cagatgcgta aggagaaaat accgcatcag gaaattgtaa acgttaatat    1440
tttgttaaaa ttcgcgttaa attttgttta aatcagctca ttttttaacc aataggccga    1500
aatcggcaaa atcccttata aatcaaaaga ataagaccgag atagggttga gtgttgttcc    1560
agtttggaac aagagtccac tattaaagaa cgtggactcc aacgtcaaag ggcgaaaaac    1620
cgtctatcag ggcgatggcc cactacgtga accatcaccc taatcaagtt ttttggggtc    1680
gaggtgccgt aaagcactaa atcggaaccc taaagggagc ccccgattta gagcttgacg    1740
gggaaagccg gcgaacgtgg cgagaaagga agggaagaaa gcgaaaggag cgggcgctag    1800
ggcgctggca agtgtagcgg tcacgctgcg cgtaaccacc acacccgccg cgcttaatgc    1860
```

```
gccgctacag ggcgcgtcgc gccattcgcc attcaggctg cgcaactgtt gggaagggcg      1920
atcggtgcgg gcctcttcgc tattacgcca gctgaattgg agcgacctca tgctatacct      1980
gagaaagcaa cctgacctac aggaaagagt tactcaagaa taagaatttt cgttttaaaa      2040
cctaagagtc actttaaaat ttgtatacac ttattttttt tataacttat ttaataataa      2100
aaatcataaa tcataagaaa ttcgcttatt tagaagtgtc aacaacgtat ctaccaacga      2160
tttgacccct ttccatcttt tcgtaaattt ctggcaaggt agacaagccg acaaccttga      2220
ttggagactt gaccaaacct ctggcgaaga attgttaatt aagagctcag atcttatcgt      2280
cgtcatcctt gtaatccatc gaattcgaat tttcaaaaat tcttactttt tttttggatg      2340
gacgcaaaga agtttaataa tcatattaca tggcattacc accatataca tatccatata      2400
catatccata tctaatctta cttatatgtt gtggaaatgt aaagagcccc attatcttag      2460
cctaaaaaaa ccttctcttt ggaactttca gtaatacgct taactgctca ttgctatatt      2520
gaagtacgga ttagaagccg ccgagcgggt gacagccctc cgaaggaaga ctctcctccg      2580
tgcgtcctcg tcttcaccgg tcgcgttcct gaaacgcaga tgtgcctcgc gccgcactgc      2640
tccgaacaat aaagattcta caatactagc ttttatggtt atgaagagga aaaattggca      2700
gtaacctggc cccacaaacc ttcaaatgaa cgaatcaaat taacaaccat aggatgataa      2760
tgcgattagt ttttagcct tatttctggg gtaattaatc agcgaagcga tgattttga        2820 tctattaaca gatatataaa tgcaaaaact gcataaccac tttaactaat actttcaaca      2880
ttttcggttt gtattacttc ttattcaaat gtaataaaag tatcaacaaa aaattgttaa      2940
tatacctcta tactttaacg tcaaggagaa aaaccccgg atccaccatg cttttgcaag      3000
cattcctttt ccttttggct ggttttgcag ccaaatatc ggccggcgat atctgtacag       3060
tggctgcacc atctgtcttc atcttcccgc catctgatga gcagttgaaa tctggaactg      3120
cctctgttgt gtgcctgctg aataacttct atcccagaga ggccaaagta cagtggaagg      3180
tggataacgc cctccaatcg ggtaactccc aggagagtgt cacagagcag gacagcaagg      3240
acagcaccta cagcctcagc agcaccctga cgctgagcaa agcagactac gagaaacaca      3300
aagtctacgc ctgcgaagtc acccatcagg gcctgagctc gcccgtcaca aagagcttca      3360
acagggagag tgtagtggc ggatcaggtt ctacgcgtag cggtggtgga ggagtagaa        3420 tcgcccggct ggaggaaaaa gtgaaaacct tgaaagctca gaactcggag ctggcgtcca      3480
cggccaacat gctcagggaa caggtggcac agcttaaaca gaaagtcatg aaccacagtg      3540
gtggtgaatt ctctacgcgt gattacaagg acgacgatga caagcatcac catcatcacc      3600
accatcacca tcactaatga tggcttaagt tcgagtaagc ttggtaccca gcttttgttc      3660
cctttagtga gggttaattc cgagcttggc gtaatcatgg tcatagctgt ttcctgtgtg      3720
aaattgttat ccgctcacaa ttccacacaa cataggagcc ggaagcataa agtgtaaagc      3780
ctggggtgcc taatgagtga ggtaactcac attaattgcg ttgcgctcac tgcccgcttt      3840
ccagtcggga aacctgtcgt gccagctgca ttaatgaatc ggccaacgcg cggggagagg      3900
cggtttgcgt attgggcgct cttccgcttc ctcgctcact gactcgctgc gctcggtcgt      3960
tcggctgcgg cgagcggtat cagctcactc aaaggcggta atacggttat ccacagaatc      4020
aggggataac gcaggaaaga acatgtgagc aaaaggccag caaaaggcca ggaaccgtaa      4080
aaaggccgcg ttgctggcgt ttttccatag gctcggcccc cctgacgagc atcacaaaaa      4140
tcgacgctca agtcagaggt ggcgaaaccc gacaggacta taaagatacc aggcgttccc      4200
ccctggaagc tccctcgtgc gctctcctgt tccgaccctg ccgcttaccg gatacctgtc      4260
```

```
cgcctttctc ccttcgggaa gcgtggcgct ttctcaatgc tcacgctgta ggtatctcag    4320
ttcggtgtag gtcgttcgct ccaagctggg ctgtgtgcac gaaccccccg ttcagcccga    4380
ccgctgcgcc ttatccggta actatcgtct tgagtccaac ccggtaagac acgacttatc    4440
gccactggca gcagccactg gtaacaggat tagcagagcg aggtatgtag gcggtgctac    4500
agagttcttg aagtggtggc ctaactacgg ctacactaga aggacagtat ttggtatctg    4560
cgctctgctg aagccagtta ccttcggaaa aagagttggt agctcttgat ccggcaaaca    4620
aaccaccgct ggtagcggtg gtttttttgt ttgcaagcag cagattacgc gcagaaaaaa    4680
aggatctcaa gaagatcctt tgatcttttc tacggggtct gacgctcagt ggaacgaaaa    4740
ctcacgttaa gggattttgg tcatgagatt atcaaaaagg atcttcacct agatcctttt    4800
aaattaaaaa tgaagtttta atcaatcta agtatatat gagtaaactt ggtctgacag    4860
ttaccaatgc ttaatcagtg aggcacctat ctcagcgatc tgtctatttc gttcatccat    4920
agttgcctga ctccccgtcg tgtagataac tacgatacgg gagggcttac catctggccc    4980
cagtgctgca atgataccgc gagacccacg ctcaccggct ccagatttat cagcaataaa    5040
ccagccagcc ggaagggccg agcgcagaag tggtcctgca actttatccg cctccatcca    5100
gtctattaat tgttgccggg aagctagagt aagtagttcg ccagttaata gtttgcgcaa    5160
cgttgttgcc attgctacag gcatcgtggt gtcacgctcg tcgtttggta tggcttcatt    5220
cagctccggt tcccaacgat caaggcgagt tacatgatcc cccatgttgt gaaaaaaagc    5280
ggttagctcc ttcggtcctc cgatcgttgt cagaagtaag ttggccgcag tgttatcact    5340
catggttatg gcagcactgc ataattctct tactgtcatg ccatccgtaa gatgcttttc    5400
tgtgactggt gagtactcaa ccaagtcatt ctgagaatag tgtatgcggc gaccgagttg    5460
ctcttgcccg gcgtcaatac gggataatac cgcgccacat agcagaactt taaaagtgct    5520
catcattgga aaacgttctt cggggcgaaa actctcaagg atcttaccgc tgttgagatc    5580
cagttcgatg taacccactc gtgcacccaa ctgatcttca gcatctttta ctttcaccag    5640
cgtttctggg tgagcaaaaa caggaaggca aaatgccgca aaaaagggaa taagggcgac    5700
acggaaatgt tgaatactca tactcttcct ttttcaatat tattgaagca tttatcaggg    5760
ttattgtctc atgagcggat acatatttga atgtatttag aaaaataaac aaataggggt    5820
tccgcgcaca tttccccgaa aagtgccacc tgggtccttt tcatcacgtg ctataaaaat    5880
aattataatt taaatttttt aatataaata tataaattaa aaatagaaag taaaaaaaga    5940
aattaaagaa aaaatagttt ttgttttccg aagatgtaaa agactctagg gggatcgcca    6000
acaaatacta ccttttatct tgctcttcct gctctcaggt attaatgccg aattgtttca    6060
tcttgtctgt gtagaagacc acacgcgaaa atcctgtgat tttacatttt acttatcgtt    6120
aatcgaatgt atatctattt aatctgcttt tcttgtctaa taaatatata tgtaaagtac    6180 gcttttgtt gaattttttt aaaccttgt ttatttttt ttcttcattc cgtaactctt    6240
ctaccttctt tatttacttt ctaaaatcca aatacaaaac ataaaataa ataaacacag    6300 agtaaattcc caaattattc catcattaaa agatacgagg cgcgtgtaag ttacaggcaa    6360
gcgatccgtc ctaagaaacc attattatca tgacattaac ctataaaaat aggcgtatca    6420
cgaggccctt tcgtc                                                    6435
```

<210> SEQ ID NO 12
<211> LENGTH: 6393
<212> TYPE: DNA

<213> ORGANISM: Artificial
<220> FEATURE:
<223> OTHER INFORMATION: Yeast Expression Vector

<400> SEQUENCE: 12

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accataattc cgttttaaga gcttggtgag cgctaggagt cactgccagg tatcgtttga     240
acacggcatt agtcagggaa gtcataacac agtcctttcc cgcaatttcc tttttctatt     300
actcttggcc tcctctagta cactctatat tttttatgc ctcggtaatg attttcattt      360
ttttttttcc acctagcgga tgactctttt tttttcttag cgattggcat tatcacataa     420
tgaattatac attatataaa gtaatgtgat ttcttcgaag aatatactaa aaaatgagca     480
ggcaagataa acgaaggcaa agatgacaga gcagaaagcc ctagtaaagc gtattacaaa     540
tgaaaccaag attcagattg cgatctcttt aaagggtggt cccctagcga tagagcactc     600
gatcttccca gaaaagagg cagaagcagt agcagaacag gccacacaat cgcaagtgat      660
taacgtccac acaggtatag ggtttctgga ccatatgata catgctctgg ccaagcattc     720
cggctggtcg ctaatcgttg agtgcattgg tgacttacac atagacgacc atcacaccac     780
tgaagactgc gggattgctc tcggtcaagc ttttaaagag gccctactgg cgcgtggagt     840
aaaaaggttt ggatcaggat ttgcgccttt ggatgaggca ctttccagag cggtggtaga     900
tctttcgaac aggccgtacg cagttgtcga acttggtttg caagggaga agtaggaga      960
tctctcttgc gagatgatcc cgcatttct tgaaagcttt gcagaggcta gcagaattac    1020
cctccacgtt gattgtctgc gaggcaagaa tgatcatcac cgtagtgaga gtgcgttcaa    1080
ggctcttgcg gttgccataa gagaagccac ctcgcccaat ggtaccaacg atgttccctc    1140
caccaaaggt gttcttatgt agtgacaccg attatttaaa gctgcagcat acgatatata    1200
tacatgtgta tatatgtata cctatgaatg tcagtaagta tgtatacgaa cagtatgata    1260
ctgaagatga caaggtaatg catcattcta tacgtgtcat tctgaacgag gcgcgctttc    1320
cttttttctt tttgctttt ctttttttt ctcttgaact cgacggatct atgcggtgtg     1380
aaataccgca cagatgcgta aggagaaaat accgcatcag gaaattgtaa acgttaatat    1440
tttgttaaaa ttcgcgttaa attttgtta aatcagctca ttttttaacc aataggccga    1500
aatcggcaaa atcccttata aatcaaaaga ataggccgag ataggggtga gtgttgttcc    1560
agtttggaac aagagtccac tattaaagaa cgtggactcc aacgtcaaag ggcgaaaaac    1620
cgtctatcag ggcgatggcc cactacgtga accatcaccc taatcaagtt ttttggggtc    1680
gaggtgccgt aaagcactaa atcggaaccc taaagggagc ccccgattta gagcttgacg    1740
gggaaagccg gcgaacgtgg cgagaaagga agggaagaaa gcgaaaggag cgggcgctag    1800
ggcgctggca agtgtagcgg tcacgctgcg cgtaaccacc acacccgccg cgcttaatgc    1860
gccgctacag ggcgcgtcgc gccattcgcc attcaggctg cgcaactgtt gggaagggcg    1920
atcggtgcgg gcctcttcgc tattacgcca gctgaattgg agcgacctca tgctatacct    1980
gagaaagcaa cctgacctac aggaaagagt tactcaagaa taagaatttt cgttttaaaa    2040
cctaagagtc actttaaaat ttgtatacac ttattttttt tataacttat ttaataataa    2100
aaatcataaa tcataagaaa ttcgcttatt tagaagtgtc aacaacgtat ctaccaacga    2160
tttgacccct ttccatcttt tcgtaaattt ctggcaaggt agacaagccg acaaccttga    2220
```

```
ttggagactt gaccaaacct ctggcgaaga attgttaatt aagagctcag atcttatcgt    2280
cgtcatcctt gtaatccatc gaattcgaat tttcaaaaat tcttacttt ttttttggatg   2340 gacgcaaaga agtttaataa tcatattaca tggcattacc accatataca tatccatata   2400
catatccata tctaatctta cttatatgtt gtggaaatgt aaagagcccc attatcttag   2460
cctaaaaaaa ccttctcttt ggaactttca gtaatacgct taactgctca ttgctatatt   2520
gaagtacgga ttagaagccg ccgagcgggt gacagccctc cgaaggaaga ctctcctccg   2580
tgcgtcctcg tcttcaccgg tcgcgttcct gaaacgcaga tgtgcctcgc gccgcactgc   2640
tccgaacaat aaagattcta caatactagc ttttatggtt atgaagagga aaaattggca   2700
gtaacctggc cccacaaacc ttcaaatgaa cgaatcaaat taacaaccat aggatgataa   2760
tgcgattagt ttttagcct tatttctggg gtaattaatc agcgaagcga tgattttga    2820 tctattaaca gatatataaa tgcaaaaact gcataaccac tttaactaat actttcaaca   2880
ttttcggttt gtattacttc ttattcaaat gtaataaaag tatcaacaaa aaattgttaa   2940
tatacctcta tactttaacg tcaaggagaa aaaccccgg atccaccatg cttttgcaag    3000
cattcctttt ccttttggct ggttttgcag ccaaaatatc ggccgaggat atcccctcga   3060
gtgaggagct tcaagccaac aaggccacac tggtgtgtct cataagtgac ttctacccgg   3120
gagccgtgac agtggcctgg aaggcagata gcagcccgt caaggcggga gtggagacca    3180
ccacaccctc caaacaaagc aacaacaagt acgcggccag cagctatctg agcctgacgc   3240
ctgagcagtg gaagtccac agaagctaca gctgccaggt cacgcatgaa gggagcaccg    3300
tggagaagac agtggcccct acagaatgtt caagtggcgg atcaggttct acgcgtagcg   3360
gtggtggagg aggtagaatc gcccggctgg aggaaaaagt gaaaaccttg aaagctcaga   3420
actcggagct ggcgtccacg gccaacatgc tcagggaaca ggtggcacag cttaaacaga   3480
aagtcatgaa ccacagtggt ggtgaattct ctacgcgtga ttacaaggac gacgatgaca   3540
agcatcacca tcatcaccac catcaccatc actaatgatg gcttaagttc gagtaagctt   3600
ggtacccagc ttttgttccc tttagtgagg gttaattccg agcttggcgt aatcatggtc   3660
atagctgttt cctgtgtgaa attgttatcc gctcacaatt ccacacaaca taggagccgg   3720
aagcataaag tgtaaagcct ggggtgccta atgagtgagg taactcacat taattgcgtt   3780
gcgctcactg cccgctttcc agtcgggaaa cctgtcgtgc cagctgcatt aatgaatcgg   3840
ccaacgcgcg gggagaggcg gtttgcgtat gggcgctct ccgcttcct cgctcactga    3900 ctcgctgcgc tcggtcgttc ggctgcggcg agcggtatca gctcactcaa aggcggtaat   3960
acggttatcc acagaatcag gggataacgc aggaaagaac atgtgagcaa aaggccagca   4020
aaaggccagg aaccgtaaaa aggccgcgtt gctggcgttt ttccataggc tcggccccc    4080 tgacgagcat cacaaaaatc gacgctcaag tcagaggtgg cgaaacccga caggactata   4140
aagataccag gcgttccccc ctggaagctc cctcgtgcgc tctcctgttc cgaccctgcc   4200
gcttaccgga tacctgtccg cctttctccc ttcgggaagc gtggcgcttt ctcaatgctc   4260
acgctgtagg tatctcagtt cggtgtaggt cgttcgctcc aagctgggct gtgtgcacga   4320
accccccgtt cagcccgacc gctgcgcctt atccggtaac tatcgtcttg agtccaaccc   4380
```

```
ggtaagacac gacttatcgc cactggcagc agccactggt aacaggatta gcagagcgag    4440
gtatgtaggc ggtgctacag agttcttgaa gtggtggcct aactacggct acactagaag    4500
gacagtattt ggtatctgcg ctctgctgaa gccagttacc ttcggaaaaa gagttggtag    4560
ctcttgatcc ggcaaacaaa ccaccgctgg tagcggtggt ttttttgttt gcaagcagca    4620
gattacgcgc agaaaaaaag gatctcaaga agatcctttg atctttcta cggggtctga     4680 cgctcagtgg aacgaaaact cacgttaagg gattttggtc atgagattat caaaaaggat    4740
cttcacctag atccttttaa attaaaaatg aagttttaaa tcaatctaaa gtatatatga    4800
gtaaacttgg tctgacagtt accaatgctt aatcagtgag gcacctatct cagcgatctg    4860
tctatttcgt tcatccatag ttgcctgact gcccgtcgtg tagataacta cgatacggga    4920
gggcttacca tctggcccca gtgctgcaat gataccgcga gacccacgct caccggctcc    4980
agatttatca gcaataaacc agccagccgg aagggccgag cgcagaagtg gtcctgcaac    5040
tttatccgcc tccatccagt ctattaattg ttgccgggaa gctagagtaa gtagttcgcc    5100
agttaatagt ttgcgcaacg ttgttgccat tgctacaggc atcgtggtgt cacgctcgtc    5160
gtttggtatg gcttcattca gctccggttc ccaacgatca aggcgagtta catgatcccc    5220
catgttgtga aaaaaagcgg ttagctcctt cggtcctccg atcgttgtca gaagtaagtt    5280
ggccgcagtg ttatcactca tggttatggc agcactgcat aattctctta ctgtcatgcc    5340
atccgtaaga tgcttttctg tgactggtga gtactcaacc aagtcattct gagaatagtg    5400
tatgcggcga ccgagttgct cttgcccggc gtcaatacgg gataataccg cgccacatag    5460
cagaacttta aaagtgctca tcattggaaa acgttcttcg gggcgaaaac tctcaaggat    5520
cttaccgctg ttgagatcca gttcgatgta acccactcgt gcacccaact gatcttcagc    5580
atcttttact ttcaccagcg tttctgggtg agcaaaaaca ggaaggcaaa atgccgcaaa    5640
aaagggaata agggcgacac ggaaatgttg aatactcata ctcttccttt tcaatatta    5700 ttgaagcatt tatcagggtt attgtctcat gagcggatac atatttgaat gtatttagaa    5760
aaataaacaa ataggggttc cgcgcacatt tccccgaaaa gtgccacctg gtccttttc    5820 atcacgtgct ataaaaataa ttataattta aattttttaa tataaatata taattaaaa    5880 atagaaagta aaaaaagaaa ttaaagaaaa aatagttttt gttttccgaa gatgtaaaag    5940
actctagggg gatcgccaac aaatactacc ttttatcttg ctcttcctgc tctcaggtat    6000
taatgccgaa ttgtttcatc ttgtctgtgt agaagaccac acacgaaaat cctgtgattt    6060
tacattttac ttatcgttaa tcgaatgtat atctatttaa tctgcttttc ttgtctaata    6120
aatatatatg taaagtacgc ttttgttga aattttttaa acctttgttt atttttttt     6180 cttcattccg taactcttct accttcttta tttactttct aaaatccaaa tacaaaacat    6240
aaaaataaat aaacacagag taaattccca aattattcca tcattaaaag atacgaggcg    6300
cgtgtaagtt acaggcaagc gatccgtcct aagaaaccat tattatcatg acattaacct    6360
ataaaaatag gcgtatcacg aggccctttc gtc                                 6393
```

TRIPLE-MODE SYSTEM FOR ANTIBODY MATURATION, SURFACE DISPLAY AND SECRETION

CROSS-REFERENCE TO RELATED APPLICATIONS

This application claims benefit of U.S. Provisional Patent Application Ser. No. 62/509,360 filed May 22, 2017, the content of which is incorporated herein in its entirety.

This invention was made with government support under one or more of R43GM10651901-High Throughput Camelid Antibody Screening As Drug Discovery Platform; R44GM10651902-High Throughput Camelid Antibody Screening As A Drug Discovery Platform; and R43GM11501101-High Throughput Approach For Generating Human Monoclonal Antibodies, all awarded by the National Institute of Health. The government has certain rights in the invention.

FIELD OF THE INVENTION

The present invention relates generally to a polypeptide display system on a eukaryotic cell surface for identifying, producing and characterizing binders to a target of interest. The eukaryotic system disclosed can facilitate simultaneous maturation, display and secretion of protein binders to a target of interest.

SEQUENCE LISTING STATEMENT

Filed herewith is a Sequence Listing (name: ABZ002_ST25.txt; created: May 15, 2018; sized: 60 KB), The content of that Sequence Listing is incorporated herein by reference in its entirety. Appended hereto is a written (pdf) version of the Sequence Listing, the content of which is identical to the above recited machine readable (txt) version.

BACKGROUND OF THE INVENTION

Antibodies have been widely accepted for treatment of a variety of diseases, including cancer, arthritis and infectious diseases. Currently more than 300 monoclonal antibody-based drugs are in clinical trials. The predominant advantage of antibody-mediated therapy is its high specificity, facilitated by direct binding to the target(s) for neutralization or elimination (KRAEBER-BODERE et al. 2014). As of Nov. 10, 2014, forty-seven monoclonal antibody products have been approved for medical use in the US or Europe (ECKER et al. 2015). Nevertheless development of antibodies as research reagents, diagnostics and therapeutics with high affinity and specificity remains both time-consuming and labor-intensive. Accordingly an animal-free, high throughput platform for antibody discovery and isolation would accelerate the antibody generation process.

Success in generation of highly specific antibodies in such an ex vivo system depends on the ability to establish highly diverse heavy and/or light chain libraries together with efficient screening capacity e.g., antibody clone identification, validation and antibody production.

One example of a widely used ex vivo system is phage display, in which an antibody fragment (e.g. ScFv) is expressed as a polypeptide fusion to a bacteriophage coat protein and subsequently an antibody of interest is selected by binding to immobilized biotinylated antigen.

As phage display is based on a bacterial protein expression system, it has several shortcomings. For example, some eukaryotic proteins may fold poorly in bacteria, or may require additional post-translational modifications, such as efficient formation of inter- and intra-chain disulfide bonds, which are unavailable in bacterial cells.

In a yeast surface display system, an antibody or antibody fragment (e.g. ScFv, VH, Fab or IgG) is expressed as a polypeptide fusion to a cell membrane anchor protein and subsequently an antibody of interest is selected by binding to immobilized biotinylated antigen in biological panning or by Fluorescence-Activation Cell Sorting or FACS.

In one example of a yeast surface display system, an antibody fragment is fused with yeast 87 amino acid AGA2 membrane protein (Uniprot number P32781, SEQ ID NO:1). Secreted antibody-AGA2 polypeptides are retained on the cell surface thanks to heterodimerization of AGA2 with the yeast membrane anchor protein AGA1 (Uniprot number P32323, SEQ ID NO:2).

To address the lack of protein secretion in eukaryotic display systems, several dual-mode display and secretion systems have been developed, in which cells can produce antibodies that are simultaneously displayed on the cell surface and secreted into the media. The secretion-and-capture system couples antibodies to the host cell surface, e.g., by biotin, where in vivo biotinylated protein of interest is captured onto the avidinated surface of the parent cell (RAKESTRAW et al. 2011). As secreted biotinylated antibodies can bind non-selectively to all avidinated cells, this system exhibits a high incidence of cross-contamination between antibody clones. Similar cross-contamination problems are observed in other systems where the full length secreted antibody is tethered on the host cell surface by binding an immunoglobulin binding protein (RHIEL et al. 2014 and U.S. Pat. No. 9,260,712) that is fused to a cell surface anchor protein.

A dual-mode surface, Fc-bait full antibody display system (SHAHEEN et al. 2013 and U.S. Pat. No. 9,365,846) addresses the cross-contamination problem. In this system, host cells will produce both full IgG antibody and antibody Fc fragment fused with a cell membrane anchor. The latter serves as a bait to capture monovalent antibody fragments. Bivalent IgG antibodies are secreted. As the yeast endoplasmic reticulum (ER), is not equipped for efficient and large scale folding of complex proteins, such as full length human antibodies (DE RUIJTER et al. 2016) the yield of secreted antibody is very low.

Application of the dual-mode surface, Fc-bait full antibody display system to mammalian cell surface display will address the full IgG secretion efficiency issues. Mammalian cell surface systems, however, have several shortcomings, including the cost, experimental time related to mammalian cell cultures as well as the level of antibody library diversity.

Thus, there is a need for an antibody generation system that provides high diversity of antibody repertoire, efficient display of antibodies on the cell surface and an option to secrete antibodies into the media, and that will therefore significantly increase the speed, reduce the cost and improve success of the antibody generation process.

Success in generation of highly specific antibodies in an ex vivo system depends on the ability to establish highly diverse heavy and/or light chain libraries together with efficient screening capacity. Currently ex vivo non-mammalian approaches for generating antibodies such as phage display (HAWKINS et al. 1992), yeast surface display (BODER and WITTRUP 1997; BODER and WITTRUP 2000), ribosome display (HANES and PLUCKTHUN 1997; HE and TAUSSIG 1997), RNA display (REIRSEN et al. 2005), and mammalian cell display (BEERLI et al. 2008) are not intrinsically capable of affinity maturation because they lack the capacity to effect somatic hypermutation. Alternatively, error-prone-PCR followed by labor-intensive sub-library re-cloning steps are generally incorporated into all current ex vivo systems to generate high-affinity antibodies (CHAO et al. 2006 and U.S. Pat. No. 8,691,730). This method is easily doable if the antibody is expressed by a single gene such as in the single-chain variable fragment (scFv) format. When antibodies consist of separate light and heavy chain genes, error-prone PCR sub-libraries have to be constructed for each antigen-specific clone to maintain the correct heavy-light chain pairing. Otherwise random pairing of a light chain from one active antibody with a heavy chain from a different clone will not likely generate again a target-specific antibody.

There is a continuing need in the art for improving the generation of specific antibodies. This invention is to a novel technology platform that combines antibody maturation, cell surface antibody display, and antibody secretion in one system. The invented system can be used for polypeptide library diversification, protein maturation and screening of binder proteins with modified affinity to another molecule. Advantages of this invention include a low cost, rapid growth eukaryotic protein expression and a surface display system with ease of culture and culture maintenance, facile manipulation and genetic engineering. Moreover, yeast mating allows random combination of antibody heavy chain and light chain libraries to form a combined library with highly diverse random H/L combinations, as is known in the art.

In an embodiment of the invention, the expression of lamprey CDA1 (Uniprot number A5H718, SEQ ID NO:3)—the most powerful deaminase mutator of DNA in yeast—which can be in combination with the chemical supermutagen HAP—allows rapid library diversification. In an embodiment of the invention, the expression of any deaminase mutator allows rapid library diversification.

In an embodiment of the invention, an antibody in vivo matured and complexed with membrane anchored bait can be expressed on the surface of the host cell, and/or while instead complexed with a soluble bait the matured antibody can be secreted from the host cell providing effective means for antibody maturation and identification.

In an embodiment of the invention, the use of diploid and/or polyploid yeast strains versus the normally used haploid yeast version protects yeast cells from lethal mutation damage due to the presence of two or more copies of essential genes. With selection methods, such as biological panning, Fluorescence Assisted Cell Sorting (FACS) for cell sorting or ELISA for secreted active antibody validation, yeast cells expressing functional binders can be quickly identified and isolated. Such methods can be used in combination.

SUMMARY OF THE INVENTION

The present invention provides for example a triple-mode yeast-based display system that does not suffer from shortcomings of currently available systems. In the present invention in vivo matured binders are displayed on the cell surface and secreted into media. The binder-displaying cells discovered by surface display screening can be turned into binder-secreting cells while preserving the protein sequence and integrity.

The present invention provides for example a triple-mode system of (i) maturation, (ii) surface display and (iii) secretion comprising: an eukaryotic host cell (for example, without limitation, a yeast *Saccharomyces cerevisiae*) engineered for (a) for antibody self-diversification; (b) expressing a membrane-anchored bait—for example, without limitation, *S. cerevisiae* AGA1 or functional fragment thereof; (c) expressing a soluble bait—for example, without limitation AGA1 without membrane anchor AGA1 N-terminal fragment of amino acids 1-149 (SEQ ID NO:4); (d) expressing one or more polynucleotides encoding a protein scaffold that is fused to a prey polypeptide that binds bait (for example, without limitation, *S. cerevisiae* AGA2). The formation of a heterodimer between anchored bait (e.g., AGA1) or soluble bait (e.g., AGA1 N-terminal fragment) with prey polypeptide-fused scaffold-encoding polypeptides will result in either scaffold display or scaffold secretion, respectively. In an embodiment of the invention, the isolated host yeast cells are engineered to enhance protein secretion (see infra Table 3). In an embodiment of the invention polynucleotides are operably associated with a regulatable promoter (for example, without limitation, a Gal1/10 promoter, an ADH1 promoter or a CUP1 promoter).

The present invention also provides for example mutagenic cytidine deaminase (for example, without limitation, PmCDA1 (SEQ ID NO:3) or functional fragment thereof; an anchored bait polypeptide, e.g., yeast AGA1 or functional fragment thereof; and a soluble bait, e.g. yeast AGA1 N-terminal fragment lacking of a membrane anchor such as without limitation AGA1 (SEQ ID NO:2) N-terminal fragment of amino acids 1-149 (SEQ ID NO:4). The scope of the present invention includes a host cell (e.g., a eukaryotic host cell such as *Saccharomyces*, e.g., *Saccharomyces cerevisiae*) expressing one or more polynucleotides encoding a scaffold protein (such as immunoglobulin heavy chain variable region (e.g., from a library), which can be in combination with immunoglobulin light chain variable region (e.g., from a library)) fused with prey polypeptide. In an embodiment of the invention, a host cell of the present invention is capable of expressing anchored bait, soluble bait and binder polypeptides.

The bait and prey polypeptides are preferably the subunits of two subunit export proteins that fold together strongly during synthesis and export. In embodiments, the subunits are disulfide linked. As such, those of skill will recognize the peptide portions needed for linkage to the bait polypeptide to the cell surface can be provided by another protein. As such, AGA2 can be fused (with a linker as needed) to the signal sequence for membrane association from another protein to serve as the bait, with AGA1 (without cell surface anchor) serving as prey. In one useful embodiment, IL-12A (Uniprot number P29459) and IL-12B (Uniprot number P29460) serve as either bait or prey. The cell surface anchor for these IL-12 polypeptides can come, for example, from human or mouse sequence providing surface anchors.

The present invention can comprise for example a host cell (e.g., *Saccharomyces* such as *Saccharomyces cerevisiae*) comprising sea lamprey cytidine deaminase e.g., PmCDA1 or functional fragment thereof located inside the cell, an anchored bait (e.g., AGA1) complexed with an prey/antigen-binding fragment (scaffold protein), e.g., located at the host cell surface by a cell surface anchor (e.g., AGA1); soluble bait (e.g., N-terminal fragment of AGA1, such as amino acid 1 to amino acid 149 fragment) complexed with an prey/protein scaffold (e.g., antigen-binding fragment), secreted by a cell into media; optionally wherein the AGA2/protein scaffold is bound to an antigen; optionally comprising an antibody or antigen-binding fragment thereof that comprises the immunoglobulin light and heavy chain of the AGA2/antigen-binding fragment; for example, wherein the host cell comprises one or more polynucleotides encoding e.g., the sea lamprey cytidine deaminase, the anchored bait, soluble bait, the prey/scaffold polypeptides or light chain immunoglobulin and/or the heavy chain immunoglobulin.

The present invention also provides for example a method for maturating and identifying: (i) an antibody or antigen-binding fragment thereof that binds specifically to an antigen; or (ii) a polynucleotide encoding an immunoglobulin heavy chain of said antibody or fragment (e.g., from a library) and/or a polynucleotide encoding an immunoglobulin light chain of said antibody or fragment (e.g., from a library); comprising (A) cultivating a culture of a eukaryotic host cell (e.g., Sacccharomyces such as S. cerevisiae) comprising (a) a polynucleotide encoding recombinant DNA that constitutively or inducibly expresses a cytosine deaminase; and (b) a bait (such as immunoglobulin light chain (e.g., from a library)); and (c) a prey sequence-fused polynucleotide encoding an immunoglobulin heavy chain (e.g., from a library); and (d) an anchored bait such as an AGA1 or it functional fragment thereof; and (e) a soluble bait such as an N-terminal fragment of AGA1 without membrane anchor such as AGA1 fragment of AA1-AA149; wherein, an anchored bait complexed with an prey/antigen-binding fragment, e.g., located at the host cell surface by a cell surface anchor (e.g., AGA1); wherein, soluble bait (e.g., AGA1 fragment of AA1-AA149) complexed with an prey/antigen-binding fragment, secreted by a cell into media; and (B) contacting cell culture with a mutagen; (C) determining if said anchored bait/prey/antigen-binding fragment displayed on cell surface specifically binds to said antigen, such as by FACS; and (D) further determining if said secreted bait/prey/antigen-binding fragment binds to said antigen, such as by ELISA.

The present invention also provides for example a method for making an antibody display system comprising: (a) an eukaryotic host cell (e.g., Saccharomyces such as Saccharomyces cerevisiae); and (b) a polynucleotide encoding recombinant DNA that constitutively or inducibly expresses a cytosine deaminase; and (c) a membrane anchored bait such as yeast AGA1 or functional fragment thereof; and (d) a soluble bait such as an N-terminal fragment of AGA1 (e.g., AGA1 fragment of AA1-AA149); and (e) one or more polynucleotides encoding a scaffold protein (e.g., immunoglobulin heavy chain variable region) that is fused to prey (e.g., S. cerevisiae AGA2); and (f) one or more polynucleotides encoding a scaffold protein (e.g., immunoglobulin light chain variable region (e.g., from a library)).

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only illustrative embodiments of this invention and are therefore not to be considered limiting of its scope, for the invention may admit to other equally effective embodiments.

FIGS. 2A, 2B, 2C, 2D and 2E present vectors for expressing polypeptide constructs;

FIG. 3A and FIG. 3C patch test and spot test FIG. 3B of forward mutations in the yeast CAN1 gene induced by overexpression of full length cytosine deaminase PmCDA1 (FIG. 3A), various variants of PmCDA1 and PmCDA2 (FIG. 3C) and exposure to the replication fidelity compromising compound HAP (FIG. 3B). Left sides—no inducers are present; Right side—yeast are exposed to inducers. As shown in FIG. 3C, only PmCDA1 (SEQ ID NO:3), not PmCDA2 (SEQ ID NO:5) induces hypermutation.

Figure 1A:
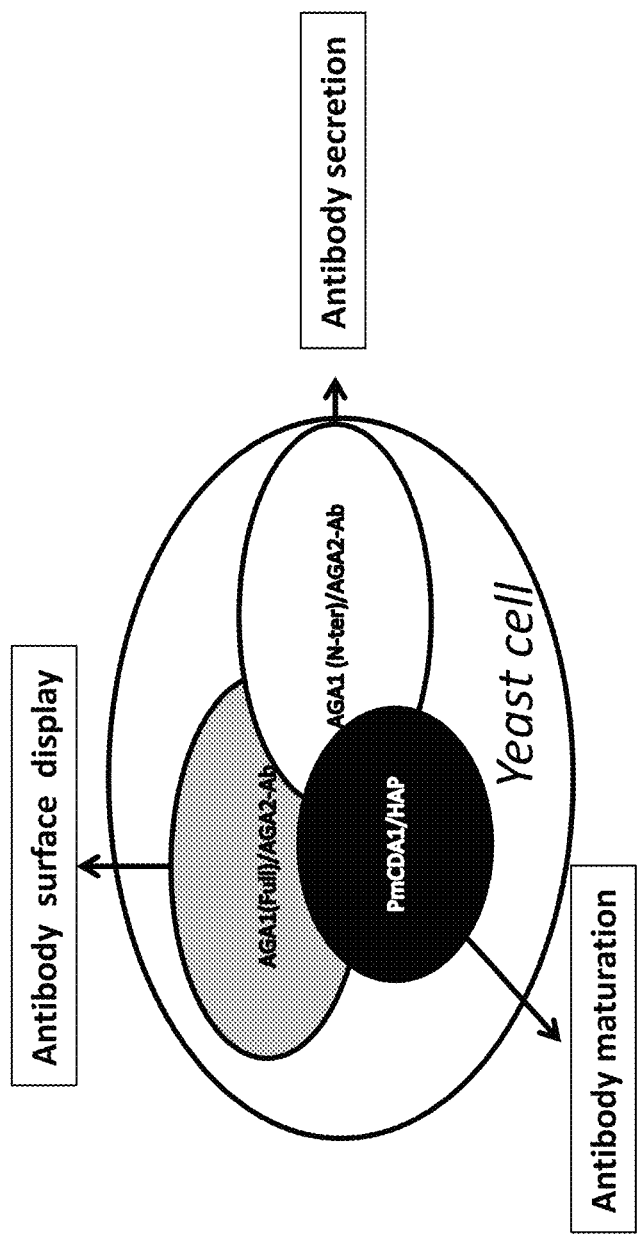
FIG. 1A is a schematic representation of yeast-based triple mode system which shows three exemplary components.

To facilitate understanding, identical reference numerals have been used, where possible, to designate comparable elements that are common to the figures. The figures are not drawn to scale and may be simplified for clarity. It is contemplated that elements and features of one embodiment may be beneficially incorporated in other embodiments without further recitation.

DETAILED DESCRIPTION

In accordance with the present invention, a triple-mode display system that simultaneously matures, displays and secretes a binder is provided to produce protein scaffolds reactive to a specific target. In a preferred aspect of the invention, an antibody discovery method is provided which enables isolating target-specific antibodies starting from a scaffold library.

Figure 1B:
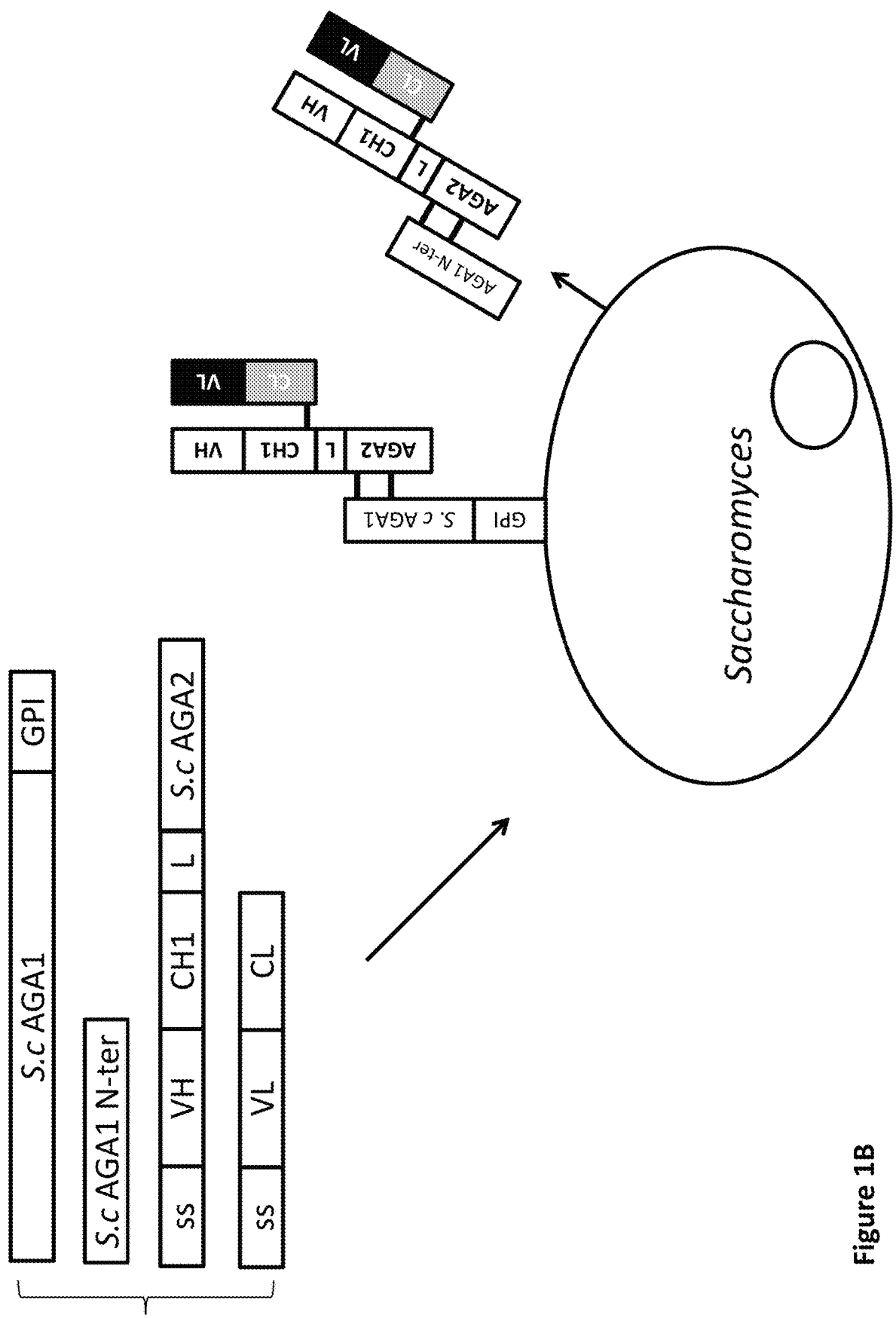
FIG. 1B shows two components for antibody display and secretion are described in more detail.

FIG. 1A is a schematic representation of yeast-based triple mode system, shown with three exemplary components. Two exemplary components for antibody display and secretion are described in more detail in FIG. 1B. The third component can for example comprise expression of Petromyzon marinas sea lamprey PmCDA1 protein (Uniprot A5H718, SEQ ID NO:3), exposure to 6-N-hydroxylaminopurine (HAP) and a yeast host strain engineered to enhance the mutator effect of PmCDA1 and HAP. FIG. 1B is a schematic representation of an exemplary yeast dual-mode antibody display system. The exemplary membrane anchor is yeast full length AGA1 protein containing a GPI anchor to the cell wall. When co-expressed in the same host with a secretable AGA2-fused protein scaffold (e.g., antibody Fab fragment), the AGA1 (the anchored bait) heterodimerizes prior to secretion in the ER with the AGA2 portion of the scaffold constructs, forming two disulfide bridges. Thus, in this instance antibody Fab will be displayed on cell surface. The soluble bait is an N-terminal fragment of AGA1 (which lacks of the GPI-anchor amidated glycine at the position 699 of AGA1). When the soluble bait is co-expressed in the same host with a secretable AGA2-fused antibody scaffold, it heterodimerizes with AGA2-fused scaffolds, resulting in secretion of the antibody Fab fragment into the culture medium.

Figure 2B:
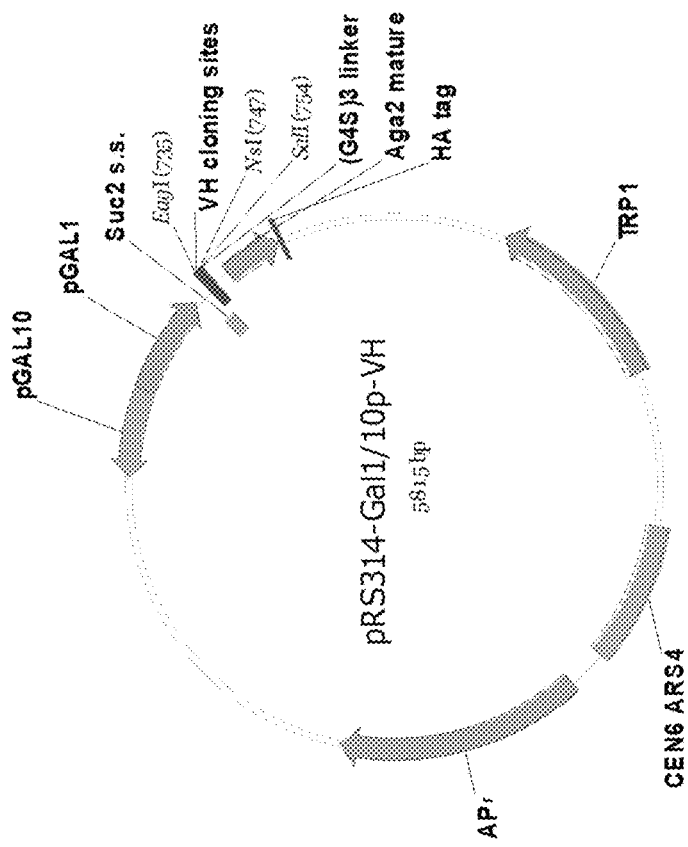
Figure 2A:
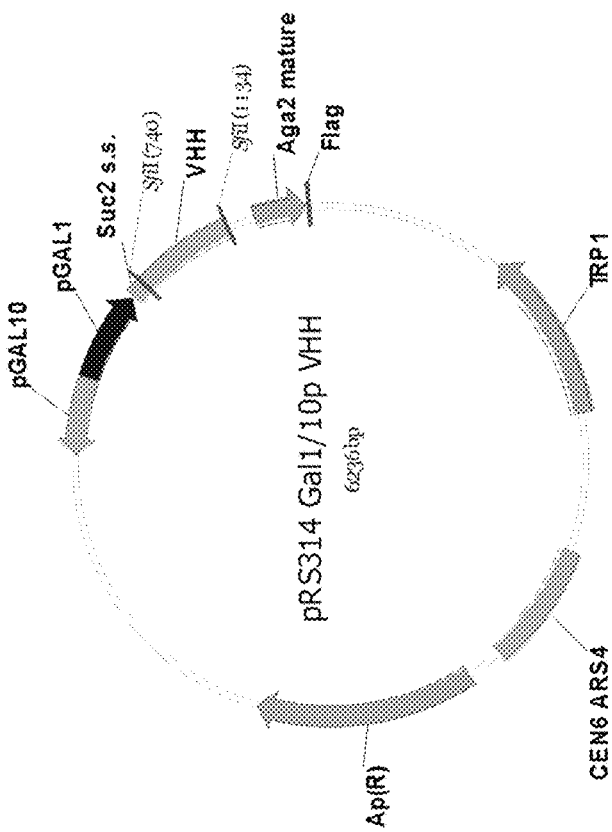

FIGS. 2A, 2B, 2C, 2D and 2E present vectors for expressing the first polypeptide constructs. FIG. 2A is representative of one camelid VHH cloned in frame with yeast invertase secretory signal at the N-terminus and membrane anchor AGA2 at the C-terminus (SEQ ID NO:6; 1-19=secretory signal, 23-149=VHH, 190-258=anchor providing segment). A gene encoding a camelid heavy chain single domain variable was cloned directionally into Sfil-Sfil sites. The fusion construct is expressed under a galactose inducible promoter, Gal1/10. This yeast-E. coli centromeric shuttle plasmid contains TRP1 as a yeast transformation marker.

SEQ ID NO:8: Nucleotide sequence of the yeast replicative vector for expression and display camelid VHH antibody on yeast cell surface as presented in FIG. 2A. SEQ ID NO:9: Nucleotide sequence of the yeast replicative vector for expression and display human heavy chain VH antibody on yeast cell surface as presented in FIG. 26. SEQ ID NO:10: Nucleotide sequence of the yeast replicative vector for expression and display the first construct, human antibody heavy chain, of human Fab fragment as presented in FIG. 2C. SEQ ID NO:11: Nucleotide sequence of the yeast replicative vector for expression and display the second construct, human antibody light chain kappa, of human Fab fragment as presented in FIG. 2D. SEQ ID NO:12: Nucleotide sequence of the yeast replicative vector for expression and display the second construct, human antibody light chain lambda, of human Fab fragment as presented in FIG. 2E.

FIG. 2B represents an exemplary backbone vector for expression of human heavy chain variable domains where human VH can be cloned at Eagl-Sall sites in frame with yeast invertase secretory signal at the N-terminus and membrane anchor AGA2 at C-terminus.

When the first construct is a heterodimeric protein such as an antibody Fab fragment two backbone vectors are used for co-expression—one vector (e.g., FIG. 2C) with TRP1 selection marker is for expressing antibody heavy chain; the heterodimeric partner, antibody light chain lambda or light chain kappa is expressed in vectors with HIS3 selection marker as presented for example in FIG. 2D and FIG. 2E, respectively.

Figure 3A:
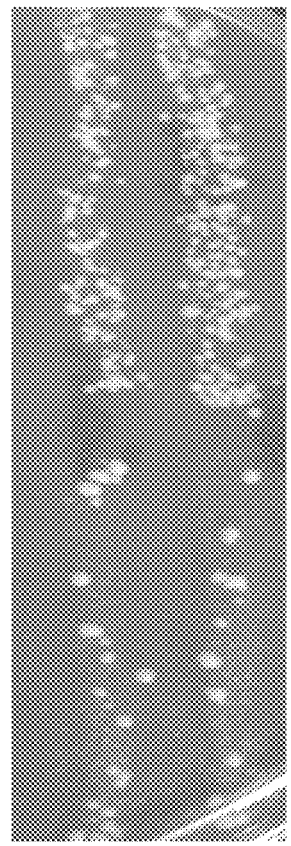
FIGS. 3A, 3B and 3C show various hypermutation tests.
Figure 3B:
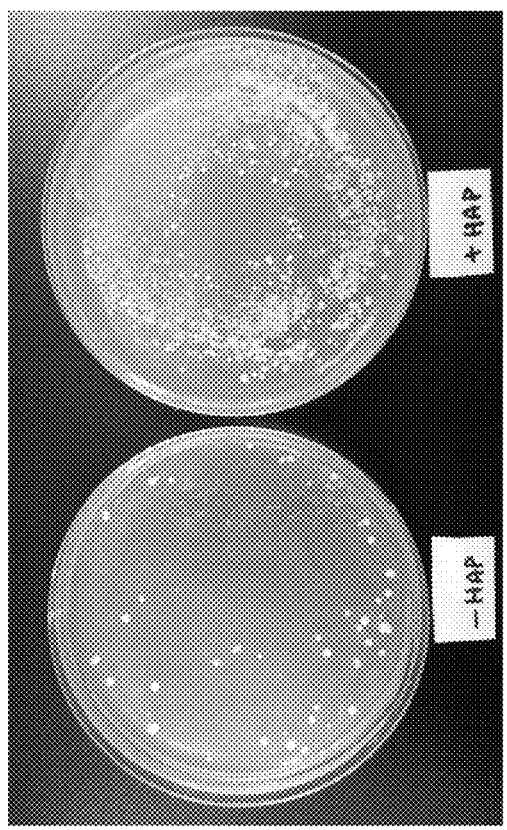
Figure 3C:
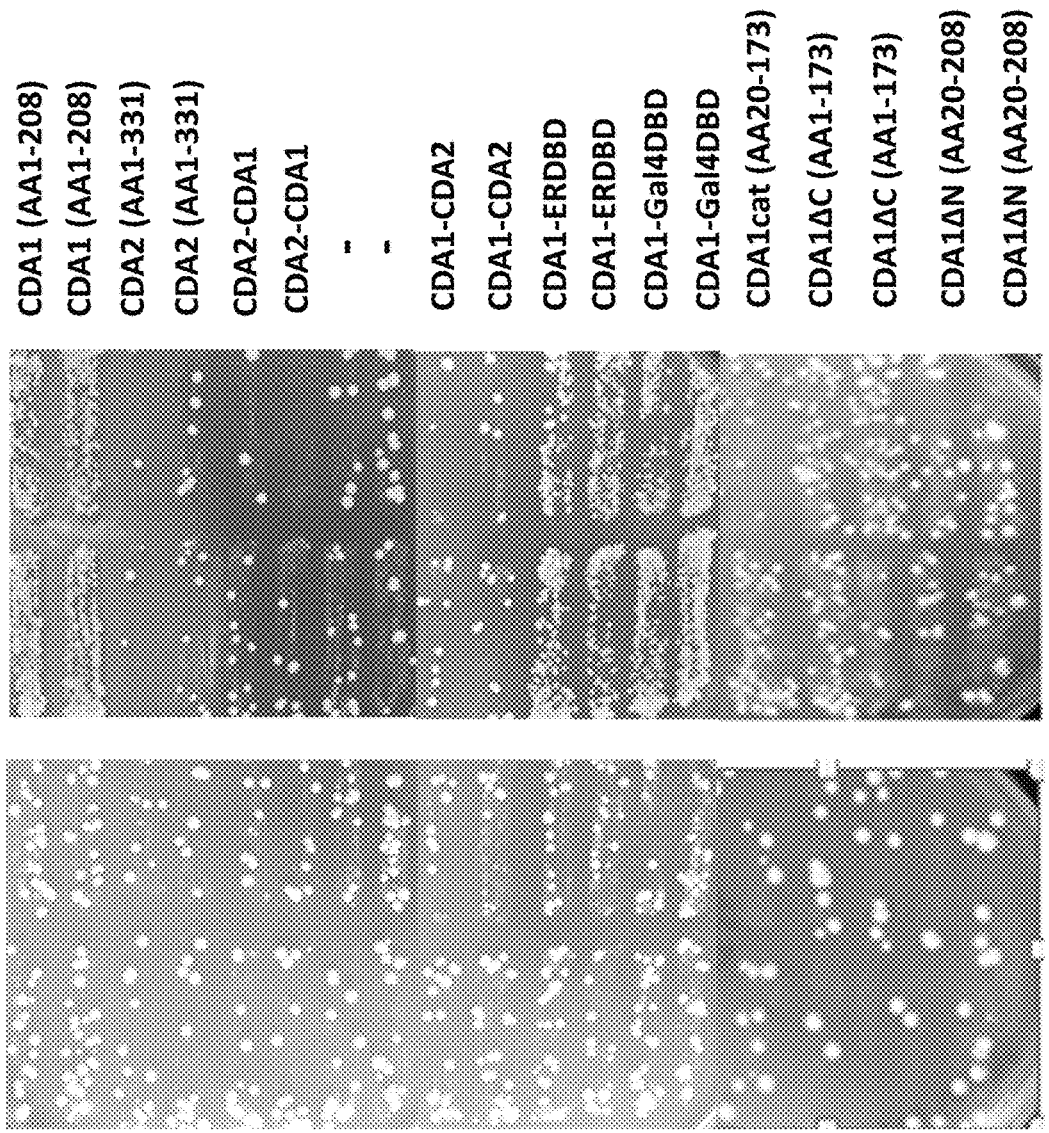

FIGS. 3A, 3B and 3C show various hypermutation tests. FIG. 3A and FIG. 3C show patch tests and FIG. 3B shows spot test of forward mutations in the yeast CAN1 gene induced by overexpression of full length cytosine deaminase PmCDA1 (FIG. 3A), various variants of PmCDA1 and PmCDA2 (FIG. 3C) and exposure to the replication fidelity compromising compound HAP (FIG. 3B). Left sides—no inducers are present; Right side—yeast are exposed to inducers. Various forms of cytidine deaminase mentioned in FIG. 3C are described in more detail in Tran et al., US20170183645A1, filed 15 Dec. 2016, the content of which, particularly as to protein sequence, is incorporated herein in its entirety.

Figures 4A, 4B:
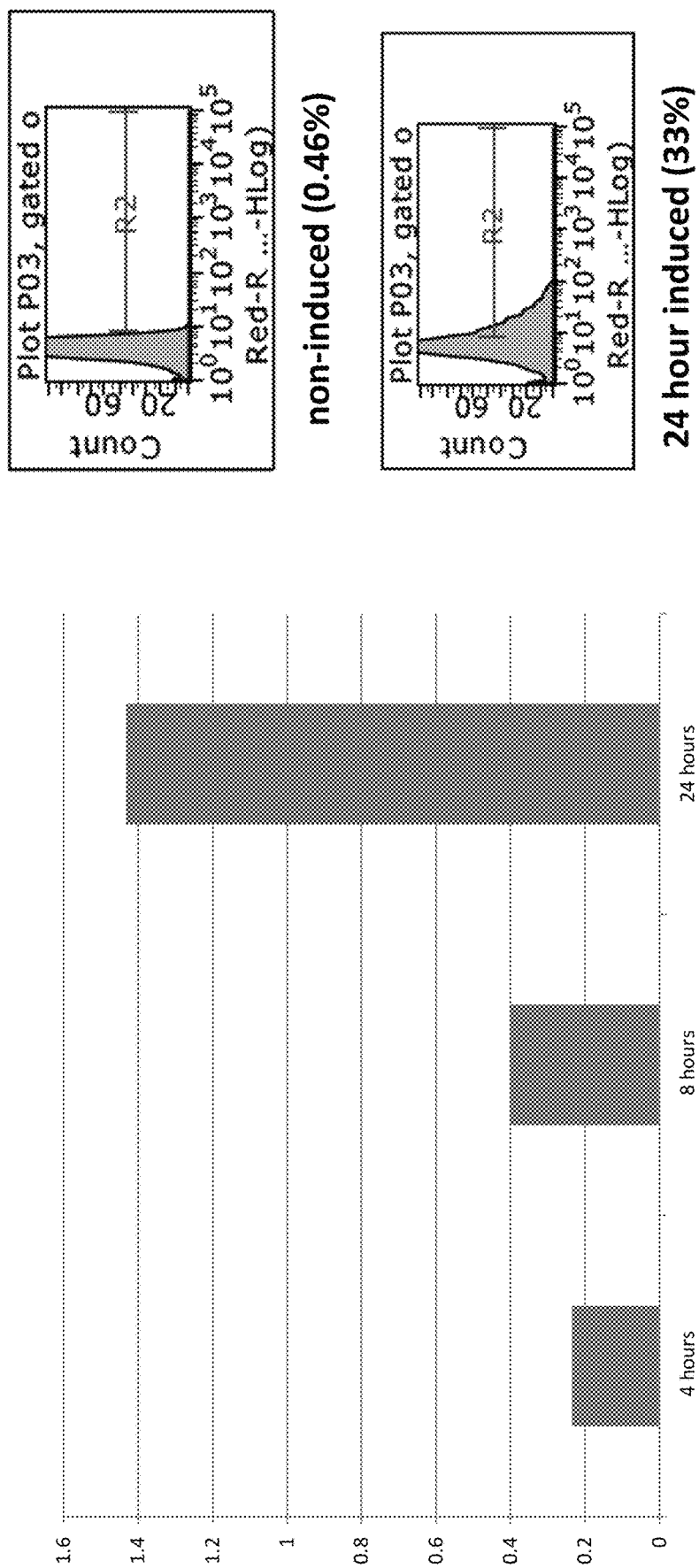
FIGS. 4A and 4B present data obtained in the double-mode system: anti-HER2 antibody Fab fragment secreted into the media detected by ELISA (FIG. 4A) and displayed on cell surface monitored by cytoflow (FIG. 4B).

FIGS. 4A and 4B present data obtained in the double-mode system: anti-HER2 antibody Fab fragment secreted into the media detected by ELISA (FIG. 4A) and displayed on cell surface monitored by cytoflow (FIG. 4B).

Figure 5:
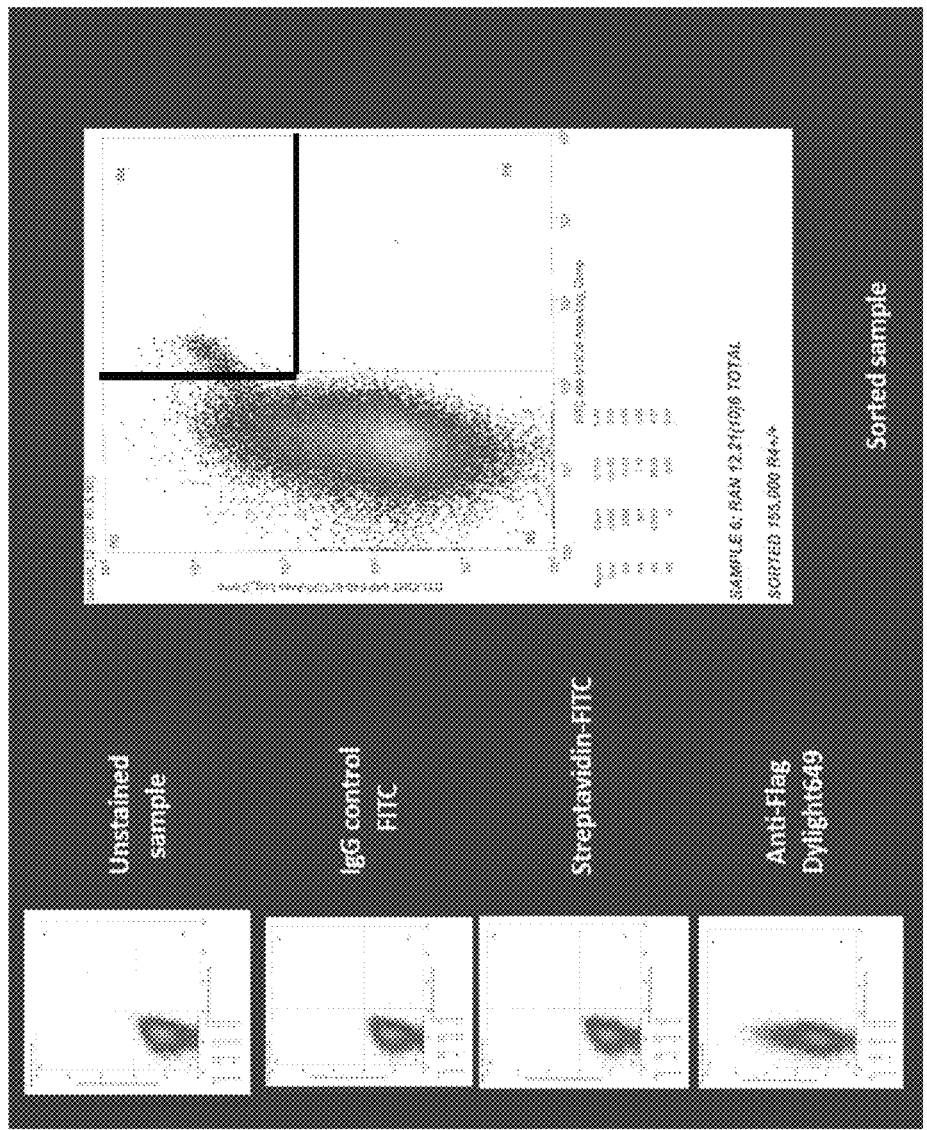
FIG. 5 shows graphs showing that the diversification and panning system of the invention efficiently sorts a cell population expressing camelid antibodies with high affinity binding to H5N1 neuraminidase target. The enriched library is labeled with anti-FLAG Dylight649 and NA-biotin/streptavidin-PE to monitor the VHH display efficiency and activity to NA. The double-positive sorted cell fraction is indicated.
Figure 6:
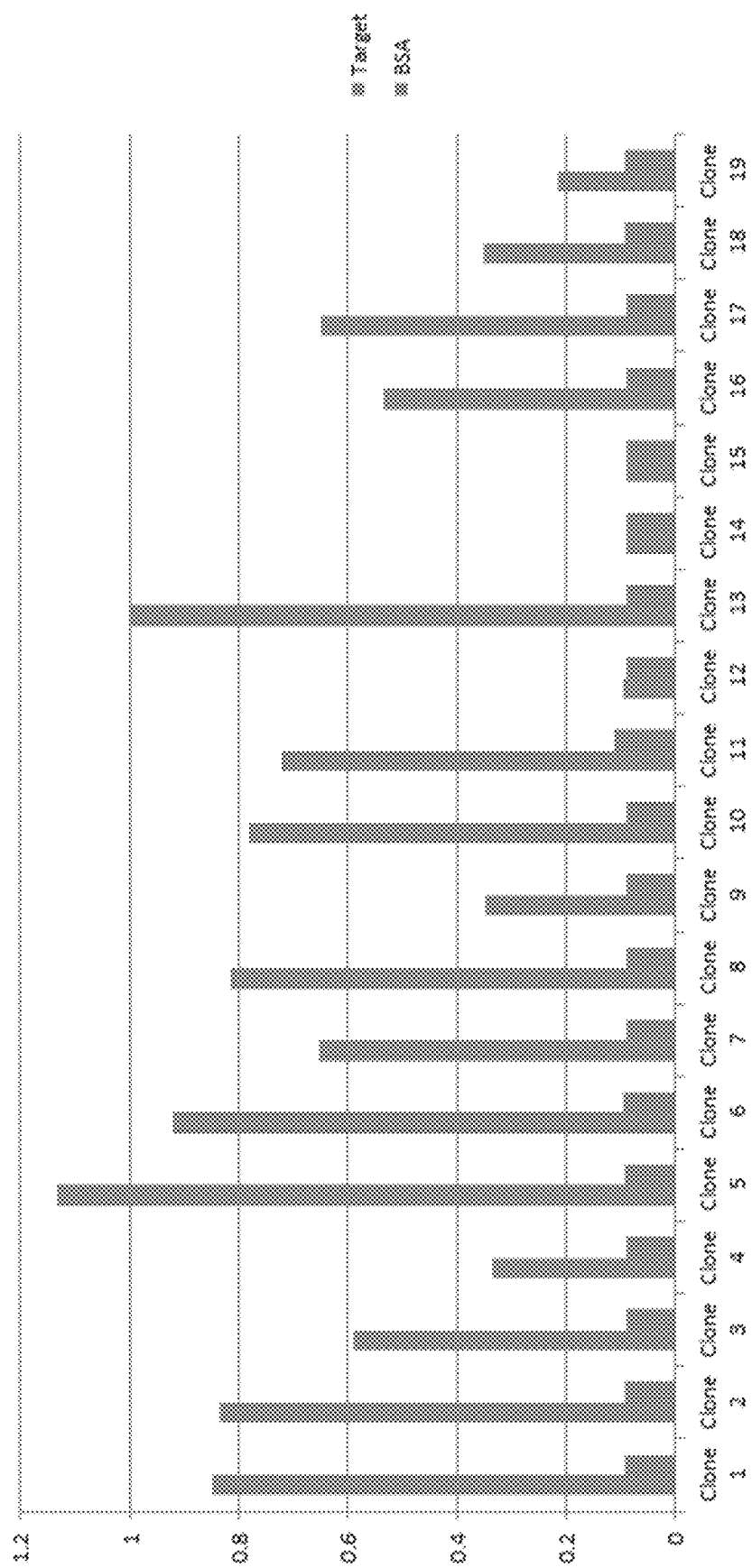
FIG. 6 presents a graph showing that the activity of antibodies secreted by yeast cells into the media can be detected by target-specific ELISA assay.
Figure 7:
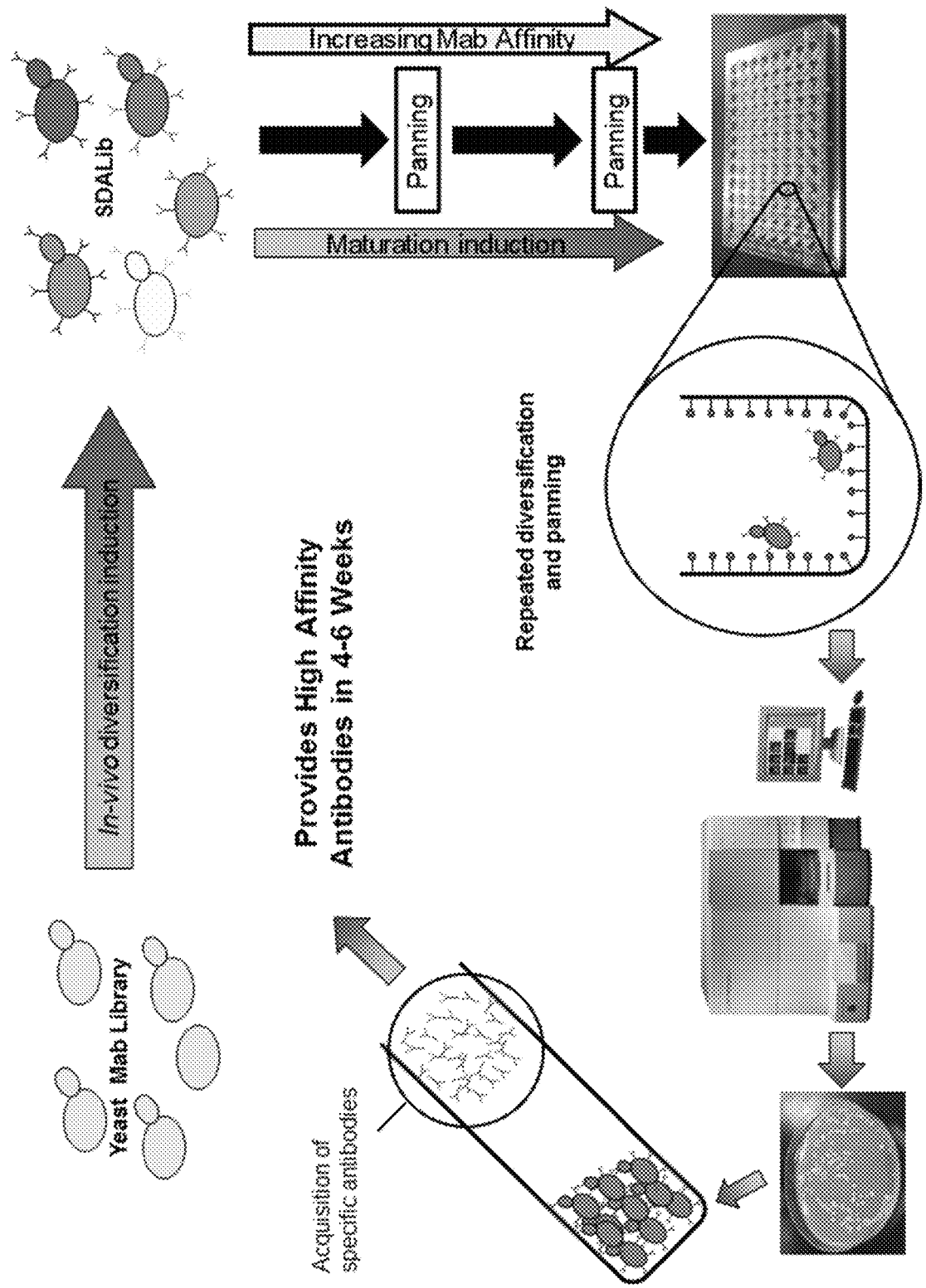
FIG. 7 is a schematic diagram of the antibody discovery system of the present invention.

FIG. 5 shows graphs showing that the diversification and panning system of the invention efficiently sorts a cell population expressing camelid antibodies with high affinity binding to H5N1 neuraminidase ("NA") target. The enriched library is labeled with anti-FLAG Dylight649 and NA-biotin/streptavidin-peroxidase to monitor the V contains the coding sequences for the polypeptide operably linked to expression control sequences which, in the appropriate host environment, facilitate transcription, processing and translation of the encoded genetic information into a protein product.

The phrase "consisting essentially of" when referring to a particular nucleotide or amino acid means a sequence having the properties of a given reference sequence. For example, when used in reference to an amino acid sequence, the phrase includes the sequence per se and molecular modifications that would not affect the basic and novel characteristics of the sequence.

As used herein, a "cloning vector" is any entity that is capable of delivering a nucleic acid sequence into a host cell for cloning purposes. Examples of cloning vectors include plasmids or phage genomes. A plasmid which replicates autonomously in a host cell is especially preferred. Alternatively, a nucleic acid molecule which stably integrates into the host cell's chromosomal DNA and is inherited by daughter cells may be employed. Optionally, such vectors include a number of endonuclease recognition sites to facilitate manipulation of the sequence in a controlled and targeted fashion. Cloning vectors of the invention may also comprise sequences conferring resistance to selection agents, often referred to herein as selectable marker genes. For example, "a marker gene" may be a gene which confers resistance to a specific antibiotic on a host cell.

As used herein, an "expression vector" is a vehicle or vector similar to the cloning vector but is especially designed to provide an environment that facilitates expression of the cloned gene product after transformation into the host. Such vectors contain regulatory elements for expression in prokaryotic and/or eukaryotic hosts as well as sequences conferring selection properties of cells containing the expression vector. Optionally, enhancer elements, termination sequences, tissue-specificity elements, and/or translational initiation and termination sites may be included.

A "host" refers to any organism or cell line that is the recipient of a cloning or expression vector. In preferred embodiments, the host of the invention is a yeast cell or a cultured animal cell such as a mammalian or insect cell. Especially preferred is the yeast host *Saccharomyces cerevisiae*.

A "transformed cell" is any cell into which (or into an ancestor of which) exogenous DNA has been introduced by means of recombinant DNA techniques or cell fusion, e.g. mating.

The terms "variant" or "derivative" in relation to AGA1 polypeptide includes any substitution of, variation of, modification of, replacement of, deletion of or addition of one (or more) amino acids from or to the original polypeptide sequence of AGA1. Preferably, nucleic acids encoding AGA1 are understood to comprise variants or derivatives thereof.

Such "modifications" of AGA1 polypeptides include fusion proteins in which AGA1 polypeptide or a portion or fragment thereof is linked to or fused to another polypeptide or molecule.

The term "homologue" as used herein with respect to the nucleotide sequence and the amino acid sequence of AGA1 may be synonymous with allelic variations in the AGA1 sequences and includes known homologues.

The term "expression" refers to the transcription of a gene's DNA template to produce the corresponding mRNA and translation of this mRNA to produce the corresponding gene product (i.e., a peptide, polypeptide, or protein). The tem "activates gene expression" refers to inducing or increasing the transcription of a gene in response to a treatment where such induction or increase is compared to the amount of gene expression in the absence of said treatment. Similarly, the terms "decreases gene expression" or "down-regulates gene expression" refers to inhibiting or blocking the transcription of a gene in response to a treatment and where such decrease or down-regulation is compared to the amount of gene expression in the absence of said treatment.

A wide variety of proteins have been subject to random mutation procedures to generate proteins that selectively bind substances. Those of skill will recognize such "scaffold" proteins with a reasonable potential for generating such binding. As with many antibodies, scaffold proteins can be composed of subunit proteins. Scaffold proteins that have been used in the past include without limitation immunoglobulin heavy chain or light chain variable regions, combinations of light and heavy chains including Fab fragments, Anticalins, fibronectin type Ill domain (e.g., Adnectins), Designed Ankyrin Repeat Protein (DARPins), Centyrins, and the like.

A "scaffold protein library" is a library of genetically diverse scaffold proteins. For example, the library can encode Adnectins.

A surface, such as for example in a polystyrene multititer plate, has a substance "bound" thereto if its association with the surface is strong enough to allow cell panning. The binding can be, but is not necessarily, covalent.

A "bait" polypeptide binds a "prey" polypeptide with sufficient binding affinity so that they can form a dimer. The dimer may be further stabilized by disulfide bond(s) between the "bait" polypeptide and the "prey" polypeptide. The "prey" polypeptide is a polypeptide fused with a scaffold protein, while the "bait" polypeptide is either fused with a cell membrane anchor or without a cell membrane anchor. Examples of potential pairs of proteins that can serve as preys and baits are presented in Table 1.

TABLE 1

Exemplary prey/soluble bait pairs that can for heterodimer or homodimers

| Prey/Genebank number | | Soluble bait/ Genebank number | | Anchors (Genebank) |
|---|---|---|---|---|
| AGA2 | P32781 | AGA1 (N-termini) | P32323 | Yeast anchors: AGA1 (P32323); CWP1 (P28319) SED1 (Q01589); GAS1 (P22146). |
| IL-12A | P29459 | IL-12B | P29460 | |
| IL-12B | P29460 | IL-12A | P29459 | |
| uteroglobin | Q9TS45 | uteroglobin | Q9TS45 | |
| IL-17A | Q16552 | IL-17F | Q96PD4 | Mammalian cell anchors: Folate receptor (P15328), CD14 (P08571); CD55 (P08174). |
| IL-17F | Q96PD4 | IL-17A | Q16552 | |
| IL-17A | Q16552 | IL-17A | Q16552 | |
| IL-17F | Q96PD4 | IL-17F | Q96PD4 | |

Membrane anchored proteins are proteins located on the surface of the cell membrane that are covalently attached to lipids embedded within the cell membrane or cross the cell membrane. Overall, there are three main types of lipid-anchored proteins which include prenylated proteins, fatty acylated proteins and glycosylphosphatidylinositol-linked proteins (GPI). An example of yeast membrane anchored protein is AGA1—anchorage subunit of a-agglutinin of a-cells; highly O-glycosylated protein with N-terminal secretion signal and C-terminal signal for addition of GPI anchor to cell wall, linked to adhesion subunit Aga2p via two disulfide bonds. Other yeast anchored proteins include CWP1, SED1, GAS1 and TIP1 (KIM et al. 2002). Examples of mammalian cell GPI-anchored proteins are GPI-proteins include cell surface receptors (e.g., folate receptor, CD14), cell adhesion molecules (e.g., NCAM isoforms, carcinoembryonic antigen variants, fasciclin I), cell surface hydrolases (e.g., 5'-nucleotidase, acetylcholinesterase, alkaline phosphatase), complement regulatory proteins (e.g., decay accelerating factor (CD55)) (ORLEAN and MENON 2007).

A dimer is a macromolecular complex formed by two, usually non-covalently bound, macromolecules such as proteins or nucleic acids. A homodimer is formed by two identical molecules (a process called homodimerization). A heterodimer is formed by two different macromolecules (called heterodimerization). The dimer may be further stabilized by a disulfide bond between macromolecules.

A disulfide bond, also called an S—S bond, or disulfide bridge, is a covalent bond derived from two thiol groups. In proteins, these bonds form between the thiol groups of two cysteine amino acids. These bonds are responsible for the stabilizing the globular structure and are the strongest type of bond that a protein can possess intrinsically and are one of the major forces responsible for holding proteins in their respective conformations, and therefore have an important role in protein folding and stability.

The "mutation rate" is the rate at which a particular mutation occurs, usually given as the number of events per gene per generation whereas "mutation frequency" is the frequency at which a particular mutant is found in the population.

"Hypermutation" or "increased mutation rate" or "increased mutation frequency" refers to the mutation of a nucleic acid in a cell at a rate above background. Preferably, hypermutation refers to a rate of mutation of between $10^{-5}$ to $10^{-3}$/base/generation. This is greatly in excess of background mutation rates, which are of the order of $10^{-9}$ to $10^{-10}$/base/generation (DRAKE et al. 1998).

The term "constitutive hypermutation" refers to the ability of certain cell lines to cause alteration of the nucleic acid sequence of one or more specific sections of endogenous or transgene DNA in a constitutive manner, that is without the requirement for external stimulation. Generally, such hypermutation is directed. In cells capable of directed constitutive hypermutation, sequences outside of the specific sections of endogenous or transgene DNA are not subjected to mutation rates above background mutation rates. The sequences which undergo constitutive hypermutation are under the influence of hypermutation-recruiting elements, as described further below, which direct the hypermutation to the locus in question. Thus in the context of the present invention, target nucleic acid sequences, into which it is desirable to introduce mutations, may be constructed, for example by replacing V gene transcription units in loci which contain hypermutation-recruiting elements with another desired transcription unit, or by constructing artificial genes comprising hypermutation-recruiting elements.

As used herein, a "mutator strain" refers to a yeast strain having a higher than naturally occurring rate of spontaneous mutation. As used herein, "mutator gene" refers to a gene which inactivation or overexpression causes a higher than naturally occurring rate of spontaneous mutation. Culturing a host comprising a mutator gene will give rise to mutational events during genome replication. An example of "mutator gene" in the present invention is UNG1 encoding Uracil DNA-glycosylase required for repair of uracil in DNA formed by spontaneous or induced cytosine deamination. When uracil-DNA glycosylase (Ung-) is lacking, the deamination of cytosine becomes a significant source of mutations (DUNCAN and MILLER 1980). Inactivation of UNG1 in yeast results in increased mutation rates (MAYOROV et al. 2005a). Another example of "mutator gene" in the present invention is sea lamprey CDA1 encoding cytidine deaminase that induces cytosine deamination on single stranded-DNA in vivo. CDA1 is considered an "active mutator gene" as its overexpression causes a higher than naturally occurring rate of spontaneous mutation in the host (ROGOZIN et al. 2007). It has been shown that overexpression of cytosine deaminases in combination with inactivation of uracil-DNA glycosylase results in synergistic mutator effects (MAYOROV et al. 2005b).

A "color marker" has optical density (in a frequency band) or fluorescence directly, has enzymatic activity that generates the same, or is adapted to selectively bind one or more substances (e.g., biotin) such that eventually in the binding substances directly have or enzymatically generate optical density or fluorescence changes.

The meaning for "identity" for polypeptides is as follows: Polypeptide embodiments (including as components of methods or yeast cell systems) further include an isolated polypeptide comprising a polypeptide having at least a 50, 60, 70, 80, 85, 90, 95, 97 or 100% identity to a polypeptide "Reference Sequence" (e.g. SEQ ID NOs:1, 2, 3, 4 or 5), wherein said polypeptide sequence may be identical to the Reference Sequence or may include up to a certain integer number of amino acid alterations as compared to the Reference Sequence, wherein said alterations are selected from the group consisting of at least one amino acid deletion, substitution, including conservative and non-conservative substitution, or insertion, and wherein said alterations may occur at the amino- or carboxy-terminal positions of the Reference Sequence or anywhere between those terminal positions, interspersed either individually among the amino acids in the Reference Sequence or in one or more contiguous groups within the Reference Sequence, and wherein said number of amino acid alterations is determined by multiplying the total number of amino acids in the Reference Sequence by the integer defining the percent identity divided by 100 and then subtracting that product from said total number of amino acids in the Reference Sequence, or:

$$n_a < x_a - (x_a \bullet y),$$

wherein $n_a$ is the number of amino acid alterations, $x_a$ is the total number of amino acids in the Reference Sequence, y is 0.50 for 50%, 0.60 for 60%, 0.70 for 70%, 0.80 for 80%, 0.85 for 85%, 0.90 for 90%, 0.95 for 95%, 0.97 for 97% or 1.00 for 100%, and is the symbol for the multiplication operator, and wherein any non-integer product of $x_a$ and y is rounded down to the nearest integer prior to subtracting it from $x_a$.

By way of example, a polypeptide sequence of the present invention may include a contiguous segment of sequence that is identical to the Reference Sequence, that is it may be 100% identical, or it may include up to a certain integer number of amino acid alterations as compared to the Reference Sequence such that the percent identity is less than 100% identity.

All ranges recited herein include ranges there between, and can be inclusive or exclusive of the endpoints. Optional included ranges are from integer values there between (or inclusive of one original endpoint), at the order of magnitude recited or the next smaller order of magnitude. For example, if the lower range value is 0.2, optional included endpoints can be 0.3, 0.4, . . . 1.1, 1.2, and the like, as well as 1, 2, 3 and the like; if the higher range is 8, optional included endpoints can be 7, 6, and the like, as well as 7.9, 7.8, and the like. One-sided boundaries, such as 3 or more, similarly include consistent boundaries (or ranges) starting at integer values at the recited order of magnitude or one lower. For example, 3 or more includes 4 or more, or 3.1 or more. If there are two ranges mentioned, such as about 1 to 10 and about 2 to 5, those of skill will recognize that the implied ranges of 1 to 5 and 2 to 10 are within the invention.

For all proteins or nucleic acids described herein with reference to a public database accession number, the database entry as of 22 May 2017 is incorporated herein in its entirety, particularly as to such sequence information and as to identification of functional domains.

II. Triple-Mode System for Maturation, Surface Display System and Secretion

Cost effective and accelerated methods for antibody discovery will have broad impact on developing diagnostic, research and therapeutic antibodies. Currently ex vivo non-mammalian surface display techniques have several short comings such as either lack of post-translational modification (e.g., phage display (HAWKINS et al. 1992), ribosome display (HANES and PLUCKTHUN 1997; HE and TAUSSIG 1997), RNA display (REIERSEN et al. 2005) or the lack of protein secretion (e.g., yeast surface display (BODER and WITTRUP 1997; BODER and WITTRUP 2000), mammalian cell display (BEERLI et al. 2008)). Several other surface systems have been developed incorporating the secretion mode for antibody production (RAKESTRAW et al. 2011; RHIEL et al. 2014; SHAHEEN et al. 2013). All these systems are not intrinsically capable of affinity maturation because they lack the capacity to affect somatic hypermutation. Table 1 summarizes the advantages and disadvantages of the current display systems, Methods that may be potentially useful for antibody discovery are set forth in Table 1,

TABLE 2

Comparison of the current antibody discovery platform with other technologies

| Display Technology | Speed | Cost | Maturation | Secretion | Problems |
|---|---|---|---|---|---|
| Triple-Mode System - Present Invention | High | Low | Yes | Yes | None |
| Phage display | High | Low | No | No | (a) |
| Yeast Display | High | Low | No | No | (b) |
| Ribosomal Display | High | Low | No | No | (a) |
| Mammalian cell display | Moderation | Mod. | No | No | (b) |
| AID + Mammalian cell display | Mod. | Mod. | Yes | No | (b) |
| Pichia pastoris Fc-bait | High | Low | No | Yes | (c) |
| Biotin/Avidinated display | High | Low | No | Yes | (d) |
| Fc/ZZ-motive display | High | Low | No | Yes | (d) |

(a) - lack of post-translational modification, secretion and maturation;
(b) - lack of antibody maturation and secretion;
(c) - lack of maturation;
(d) - cross-clone contamination, lack of maturation.

Numerous surface display techniques to generate antibodies were evaluated. As can be seen from Table 1 only the triple-mode display technology described herein meets the desired criteria of cost, speed, protein display and secretion, antibody in vivo maturation and ease of application. As antibody maturation and secretion mode is incorporated into the Triple-mode Display System, additional steps such as in vitro maturation by error-prone FOR, cloning of antibody-encoding genes into another expression system are not required.

There is a continuing need in the art for improved antibody development platforms. This invention is a novel technology platform, that comprises three components (a) antibody maturation component; (b) antibody display component; and (c) antibody secretion component. The invented system can be used for polypeptide library diversification, protein maturation and rapid screening of binder proteins with modified affinity to another molecule. Advantages of this invention include low cost, rapid growth eukaryotic protein expression and a surface display system with ease of culture, culture maintenance, facile manipulation and genetic engineering. Moreover, yeast mating allows combination of antibody heavy chain and light chain libraries to form a single library with highly diverse random H/L combinations. The expression of sea lamprey ODA—the most powerful deaminase mutator in yeast-directed to a DNA target in combination with the chemical supermutagen HAP allows rapid library diversification, and finally the use of diploid and/or polyploid yeast strains protect yeast cells from detrimental genetic damage of the induced mutagenesis due to the presence of two or more copies of essential genes.

In embodiments, in combination with Fluorescence Assisted Cell Sorting (FACS) followed by ELISA to measure activity of secreted antibodies in the cell culture media, yeast cells expressing functional binders can be quickly identified.

In accordance with the present invention, a yeast-based genetic system and methods of use, thereof are provided to facilitate antibody discovery. The methods provided herein enable the rapid and efficient maturation and isolation of antibody clones to an antigen target of interest starting from a naïve antibody library, or alternatively to improve the activity of a known protein, including antibodies.

III. Preparation of Nucleic Acid Molecules Encoding the Proteins of the Invention

A. Nucleic Acid Molecules

Nucleic acid molecules encoding the expression vectors of the invention may be prepared by two general methods: (1) They may be synthesized from appropriate chemical starting materials, or (2) they may be isolated from biological sources. Both methods utilize protocols well known in the art.

The availability of nucleotide sequence information, for the sea lamprey CDA1, yeast AGA1, AGA2 as well as for secretory signals from alpha-mating factor or yeast SUC2 gene (providing secretory signal) facilitates synthesis of DNA constructs containing such sequences, Synthetic oligonucleotides may be prepared by the phosphoramadite method employed in the Applied Biosystems 38A DNA Synthesizer or similar devices. The resultant construct may be purified according to methods known in the art, such as high performance liquid chromatography (HPLC). Long, double-stranded polynucleotides, such as a DNA molecule encoding a construct of the present invention, must be synthesized in stages due to the size limitations inherent in current oligonucleotide synthetic methods. Thus, for example, a 3 kilobase double-stranded molecule may be synthesized as several smaller segments of appropriate complementarity. Complementary segments thus produced may be ligated such that each segment possesses appropriate cohesive termini for attachment of an adjacent segment. Adjacent segments may be ligated by annealing cohesive termini in the presence of DNA ligase to construct the entire 3 kilobase double-stranded molecule. A synthetic DNA molecule so constructed may then be cloned and amplified in an appropriate vector.

In alternative embodiments of the invention, the sea lamprey CDA, yeast AGA1, AGA2 and yeast SUC2 secretory signal can be substituted with similar genes with functional homology from other biological sources. In the PmCDA1 example, suitable candidate genes for such substitution include, without limitation, lamprey cytosine deaminase mutated (modified or altered cytosine deaminases), derivatives such as a CDA1 hybrid with ER DNA binding domain (ER-DBD), which also has high mutator phentotype once expressed in yeast defective in Uracil-DNA glycosylase. In addition, one can replace PmCDA1 with cytosine deaminase from other species, including but not limited to human AID.

In the example of yeast AGA1 and AGA2 heterodimerized via disulfide bond formation in ER, they can be substituted with components of a extracellular disulfide-bridged homodimer (e.g., 10 kDa uteroglobin, Uniprot # Q9TS45) or heterodimer protein such as human IL-12 encoded by two separate genes, IL-12A (Uniprot # P29459) and IL-12B (Uniprot # P29460).

Yeast SUC2 secretory signal of the invention used for promoting protein secretion may be derived from different species not limited to *S. pombe* and *K. lactis*. It can be substituted with yeast alpha mating factor secretory signal that also functions as secretory signal.

Nucleic acid sequences encoding the components of the expression plasmids of the invention may be isolated from appropriate biological sources using methods known in the art. For example, RNA isolated from a mammalian or insect cell may be used as a suitable starting material for the generation of cDNA molecules encoding the different receptor proteins.

In accordance with the present invention, nucleic acids having the appropriate level of sequence homology with the protein coding region of the DNA molecules of the present invention may be identified by using hybridization and washing conditions of appropriate stringency. For example, hybridizations may be performed at 37° C. to 42° C. for at least six hours. Targets with greater than about 75% sequence identity would be observed using a hybridization temperature of 42° C. Such a sequence would be considered substantially homologous to the sequences of the present invention.

The nucleic acids of the invention may also be used as starting materials for the generation of sequence variants or truncation mutants of the nucleic acids of the invention using any number of synthetic and molecular biologic procedures well known in the art including, but not limited to, truncation at available restriction sites and site-directed mutagenesis techniques. Particular mutations may give rise to receptor proteins with altered characteristics such as increased or decreased ligand binding activity.

B. Fusion Proteins

In one embodiment of the invention, the antibodies of the invention are expressed in yeast as fusion proteins having a yeast secretory signal at the N-terminus. Secretory signal fusion at the N-terminus of the protein facilitates extracellular secretion of the protein following translation. After translation of recombinant proteins, the secretory signals at the N-terminus are cleaved by the host secretory pathway proteases and native proteins are released. It is widely known that the presence of the secretory signals results in secretion of proteins of interest in yeast (KJAERULFF and JENSEN 2005).

In one embodiment of the invention, the antibodies of the invention are expressed in yeast as fusion proteins with yeast AGA2 at their C-termini. As a result of heterodimerization of yeast AGA2 with yeast membrane anchor AGA1, secreted antibodies or polypeptides are retained on the yeast cell surface (BODER and WITTRUP 1997) therefore accessible to an antigen of interest located extracellularly.

In another embodiment of the invention, the hybrid membrane anchor consists of fusion of the AGA1 N-terminal fragment (AA1-149) with yeast cell wall protein CWP1 (SEQ ID NO:7; 1-149=AGA1 fragment, 173-392=CWP1). As a result of heterodimerization of yeast AGA2 used with antibody scaffolds at their C-termini with yeast AGA1 N-terminal fragment (AA1-149) (SHEN et al. 2001), secreted antibodies or polypeptides are retained on the yeast cell surface therefore accessible to an antigen of interest located extracellularly.

In another embodiment of the invention, the antibodies of the invention are expressed in yeast as fusion proteins with yeast AGA2 at their C-termini. As a result of heterodimerization of yeast AGA2 with yeast AGA1 N-terminal fragment (AA1-149) (SHEN et al. 2001) and the lack of membrane anchor, AGA2/antibodies complexed with the AGA1 fragment will be secreted extracellularly.

IV. Assay Methods and Kits

In yet another embodiment of the invention, assays are provided wherein intact cells expressing a protein of interest are grown in cell culture media containing base analogue molecules and molecules to induce expression of cytosine deaminase. After a suitable time period, the diversification of a gene or protein of interest is measured. Such diversification of a gene or protein of interest may be quantitated in any number of ways. For example, such cell systems may utilize a reporter system in which the production of the reporter signal is dependent on enzymatic or fluorescence or binding activity of the protein of interest. Numerous reporters may serve equally well in this application including but not limited to, beta-galactosidase, alkaline phosphatase, green fluorescent protein, antibody, protein scaffold and the like. Inactivation or activation of the gene of interest can be also measured as forward and reverse mutation rates. For example, mutation in the arginine permease encoding gene CAN1 confers resistance to canavanine (LANG and MURRAY 2008). The gene diversification level can be measured by Next Generation Sequencing. Furthermore, the methods of the invention may be practiced in bacterial, fungal, insect, avian, mammalian or plant cells. However, yeast-based cell systems are preferred due to low cost and the feasibility of growing yeast cells in plastic devices.

Assays for screening binders to a target of interest are also provided. Diversification of binders in the cell-based system may be followed by isolation of cells expressing modified binders reactive to a target by means of biological panning or fluorescence-activation cell sorting (FACS). Isolation of binders reactive to a target of interest can be performed as described previously (CHAO et al. 2006). In another aspect, the invention includes kits to facilitate the use of the compositions and methods disclosed herein. Exemplary kits include the expression plasmids, yeast-based scaffold libraries and yeast strains of the invention, and/or variants thereof. Also provided are cell culture media, compounds and protocols for use of the compositions of the invention for the particular application and the necessary reagents to carry out the application are also provided. Such reagents may include, but not be limited to, buffers, solvents, media and solutions.

The following protocols are provided to facilitate construction of the expression plasmids for use in the methods and kits of the present invention.

Yeast Media, Strains, Plasmids, Antibody Library

Standard yeast and E. coli media were prepared as described in detail (CHAO et al. 2006). For example, YPD composed of Yeast Extract (20 grams per liter), Peptone (20 g/liter), Dextrose (20 g/Liter) is preferred for use in the invention as most yeast strains grow in this media. Yeast selective media (complete-drop out) used to maintain plasmids is composed of yeast nitrogen base 1.7 g/L, ammonium sulfate 5 g/L, dextrose 20 g/L, different amino acids and other supplements depending on the requirements of the particular yeast strain. For example if the yeast plasmid contains the LEU2 marker, the leucine is dropped out from the media in order to select the plasmid. Other buffered selective media such as SDCAA glucose media and SGR-CAA galactose media were prepared as described in detail (CHAO et al. 2006).

Yeast strains suitable for use in the present invention include the yeast strains of opposite mating types presented in Table 2.

TABLE 3

Yeast strains of opposite mating types used for developing the triple-mode sysem

| Strains | Genotype | Application |
|---------|----------|-------------|
| A169x | Mat alpha Gal1p-AGA1/URA3 opi1::[Bsd$^R$/Cup1p-AGA1(AA1-149)] ura3-52 trp1::NatMX leu2-Δ200 his3-Δ200 lys2Δ pep4::Zeo$^R$ prbΔ1.6R can1 ung1::HygB ham1::KanMX | for transformation of DNA construct encoding light chain |
| A170x | MatA Gal1p-AGA1/URA3 ura3-52 opi1::[Bsd$^R$/Cup1p-AGA1(AA1-149)] trp1-Δ63 Gal1p-PmCDA1/LEU2 leu2 his3::Zeo$^R$ pep4-3 prb1-22 prd-407 ung1::HygB ham1::KanMX | for transformation of DNA construct encoding heavy chain |

A series of yeast expression plasmids for expression and display of a protein of interest on the yeast cell surface were constructed based on the yeast-E. coli single copy shuttle plasmid pRS314 (SIKORSKI and H$_{IETER}$ 1989). All plasmid derivatives are yeast-E. coli centromeric shuttle plasmids containing TRP1 as a yeast transformation marker. FIG. 2A depicts an exemplary plasmid pRS314_Gal1/10p_VHH of the invention that is suitable for expression and display of camelid heavy chain variable domains on the yeast cell surface. pRS314_Gal1/10p_VHH is comprised of the centromeric plasmid pRS314 (SIKORSKI and HIETER 1989), S. cerevisiae bi-directional galactose inducible promoter Gal1/10, yeast Suc2 (invertase) secretory signal, Sfil-Sfil cloning sites, linker, membrane anchor AGA2 and FLAG tag at its C-terminus. pRS314-Gal1/10p-VH (FIG. 2B) used for expressing human VH has a similar structure containing the Gal1/10 promoter, yeast Suc2 (invertase) secretory signal, Eagl-Sall cloning sites, linker membrane anchor AGA2 and HA tag at its C-terminus. In another construct variable domains are expressed as a fusion at AGA2 C-terminus.

Proteins of interest such as antibody heavy chain or light chain variable regions, protein scaffolds including, but not limited to Anticalins, fibronectin type III domain—Adnectins, camelid antibodies, Designed Ankyrin Repeat Protein or DARPins and Centyrins can be expressed and displayed on the yeast cell surface using the two vectors mentioned above.

When a protein of interest is a heterodimer such as an antibody Fab fragment, it requires two plasmids to express both partners simultaneously. For example, to express and display antibody Fab fragments, two yeast-E. coli centromeric plasmids have to be constructed to express both heavy chain and light chains. For expression of heavy chain, for example, the yeast-E. coli centromeric plasmid pRS314-Gal1/10p-Eagl-Sall plasmid (FIG. 2C) that contains the yeast Gal1/10 promoter, Suc2 invertase secretory signal, cloning sites Eagl and Sall for heavy chain VH cloning, CH1 constant domain, leucine zipper FOS followed with HA tag was constructed. The plasmid contains a TRP1 yeast transformation marker. For expression of light chain, for example, a series of plasmids derived from plasmid pRS316 (SIKORSKI and HIETER 1989) that contains a HIS3 transformation selection marker were constructed. pRS316-Gal1/10p-Eagl-BsrG1-Ck for kappa light chain (FIG. 2D) and pRS316-Gal1/10p-Eagl-XhoI-CL for lambda light chain (FIG. 2D) were constructed. These two plasmids each contain a yeast Gal1/10 promoter, Suc2 invertase secretory signal, cloning sites Eagl/BsrGl or Eagl/Xhol for light chain variable cloning, Kappa or Lambda light chain constant region, respectively, leucine zipper Jun to facilitate dimerization followed with FLAG tag for display and expression monitoring. Heteromeric formation is possible via formation of heavy chain and light chain constant domains facilitated by the leucine zipper Fos/Jun. The pRS316-based plasmid contains a HIS3 yeast transformation marker.

To display and diversify Fab fragments, heavy chain and light chain variable domains are cloned in frame at the cloning sites in the respective vectors described above, Heavy chain vectors are introduced, for example, into the A169x yeast strain by yeast transformation selecting colonies growing in media without tryptophan, Light chain vectors are introduced, for example, into the A170x strain that already contains the integrated PmCDA1 selecting colonies growing in media without histidine. A diploid is obtained by mating Trp$^+$ and His$^+$ transformants and selecting Trp$^+$ His$^+$ colonies. Genes expressing heavy chain and light chain variable domains are diversified by growing diploids in media containing galactose as a sole carbon source to induce both antibody encoding genes and the CDA1 encoding gene.

Also provided is a camelid VHH library constructed using the yeast-E. coli expression vector pRS314-Gal1/10-VHH (FIG. 2A). Complementary DNA (cDNA) derived from camelid leukocyte mRNA encoding heavy chain variable domains has been cloned in frame with the secretory signal and AGA2, cDNA library construction is well known in the art. The camelid VHH library has been introduced into the A169x yeast strains using Trp$^+$ selection. The final selfdiversifying camelid antibody library was obtained, for example, by mating A169x library with the A170x yeast strain containing the CDA gene integrated.

Exemplary Diversification Methods

A diploid host cell containing a first DNA construct having a nucleic acid molecule encoding a protein that is subjected for diversification, a second DNA construct having a nucleic acid molecule encoding cytosine deaminase, a third DNA construct having a nucleic acid molecule encoding an anchored bait and a forth construct having a nucleic acid molecule encoding a soluble bait will undergo diversification by two means either performed separately or in combination.

In the first means of diversification a host cell containing constructs of the invention is continuously grown in yeast selective media that contains promoter inducers including but not limited to (1) galactose (20 g/L) as a sole carbon source to induce the Gal1/10 promoter or (2) copper at concentrations of 100 micro molar to 1 mM to induce the Cup1 promoter. Under such conditions cytosine deaminase is expressed. Produced cytosine deaminases will convert C to U via deamination in transcriptionally active genes including a gene of interest.

In the second means of diversification, a host cell containing constructs of the invention is continuously grown in yeast selective media containing base analogues including, but not limited to 6N-hydroxylamine purine or HAP. During replication the base analog 6-N-hydroxylaminopurine (HAP) induces bidirectional GC→AT and AT→GC transitions (SHICHERBAKOVA and P$_{AVLOV}$ 1993).

As gene diversification occurs via hypermutation that is active during cell division via DNA replication, the level of diversification obtained is directly related to numbers of mutations in a gene of interest that accumulate as cells grow. Therefore the longer cells undergo diversification, the more mutations will accumulate. The present invention, accordingly, includes the method comprising the following steps for diversifying an antibody or antigen-binding fragment thereof:
  (1) Grow in a liquid culture media host cells comprising:
    (i) sea lamprey cytidine deaminase or functional fragment thereof;
    (ii) and one or more AGA2 fused antibody scaffolds;
    (iii) and membrane anchor AGA1 bait or functional fragment thereof;
    (iv) and soluble AGA1 bait or functional fragment thereof.
  (2) Allow expression of antibody scaffolds and sea lamprey CDA1;
  (3) Optionally, contact cells with mutagen, such as base analog, 6N-hydroxyaminopurine.

Methods for Identifying Antibody to a Target of Interest

In an embodiment of the invention, after the diversification step, the eukaryotic host cells expressing the anchored AGA1 bait dimerized with the AGA2/antigen-binding fragment are identified and sorted using fluorescence-activated cell sorting (FACS). For example, in an embodiment of the invention, cells expressing the anchored AGA1 bait dimerized with the AGA2/antigen-binding fragment on the cell surface are labeled with either a fluorescent antigen or biotinylated antigen/fluorescent streptavidin. The fluorescent label is detected during the FACS experiment and used as the signal for sorting. Labeled cells indicate the presence of a cell surface expressed AGA1/AGA2/antigen-binding fragment/antigen complex and are collected in one vessel whereas cells without signal are collected in a separate vessel. The present invention, accordingly, includes a method comprising the following steps for determining if an antibody or antigen-binding fragment thereof from a library specifically binds to an antigen:
  (1) Grow in a liquid culture media host cells comprising:
    (i) sea lamprey cytidine deaminase or functional fragment thereof;
    (ii) and one or more AGA2 fused antibody scaffolds;
    (iii) and membrane anchor AGA1 bait or functional fragment thereof;
    (iv) and soluble AGA1 bait of functional fragment thereof.
  (2) Allow expression of antibody scaffolds and the anchored AGA1 bait on the surface of the cells;
  (3) Optionally, enrich cells expressing binders to an antigen of interest as follows:
    (i) Label cells with biotinylated antigen;
    (ii) Collect labeled cells using streptavidin-coated magnetic particles for a one round;
    (iii) Regrow the labeled, enriched cells;
    (iv) Allow expression of antibody scaffolds and the anchored AGA1 bait on the surface of the cells;
    (v) Label cells with biotinylated antigen;
    (vi) Collect labeled cells using Avidin-coated magnetic particles for a second round.
    (vii) Regrow the labeled, enriched cells;
    (viii) Allow expression of antibody scaffolds and the anchored AGA1 bait on the surface of the cells;
    (ix) Label cells with biotinylated antigen;
    (x) Collect labeled cells using anti-biotin-coated magnetic particles for a third round
  (4) Regrow the enriched cells.
  (5) Allow expression of antibody scaffolds and the anchored AGA1 bait on the surface of the cells;
  (6) Label the cells with fluorescently labeled antigen or antigen bound to a fluorescently labeled secondary antibody;
  (7) Sort and isolate fluorescently labeled cells using FACS for one round;
  (8) Regrow the sorted cells;
  (9) Allow expression of antibody scaffolds and the anchored AGA1 bait on the surface of the cells;
  (10) Sort and isolate fluorescently labeled cells using FACS for a second round;
  (11) Regrow the labeled, sorted cells on solid culture medium so that individual cellular clones grow into discrete cellular colonies;
  (12) Identify colonies with affinity for the antigen using cytoflow analysis;
  (13) Grow cells from identified colonies in a liquid culture medium
  (14) Allow expression of a soluble AGA1 bait and antigen-binding fragments;
  (15) Isolate supernatant containing a soluble AGA1 bait complexed with secreted antigen-binding fragment thereof comprising the immunoglobulin light and heavy chains or VH1-1;
  (16) Determine affinity of secreted antibodies or antigen-binding fragments thereof, from the supernatant, for the antigen and identify clones with acceptable affinity;
  (17) Determine the nucleotide sequence of polynucleotides in the identified clones encoding the heavy and light chain immunoglobulins

NUMBERED EMBODIMENTS

The invention is further described with reference to the following numbered embodiments;

Embodiment 1. A eukaryotic cell providing a protein display, protein selection and soluble protein recovery system, comprising: a) recombinant DNA capable of expressing a mutagenic cytidine deaminase; b) recombinant DNA capable of expressing a membrane-bound version of a bait polypeptide; c) recombinant DNA capable of expressing a soluble version of the bait polypeptide; and d) recombinant DNA capable of expressing one or more polypeptides of a scaffold protein, with one or more said scaffold polypeptides operably fused to a prey polypeptide.

Embodiment 2. The eukaryotic cell of a Cell Embodiment, wherein the cytidine deaminase is sea lamprey *Petromyzon marinus* cytidine deaminase CDA1 or functional fragment thereof.

Embodiment 3. The eukaryotic cell of a Cell Embodiment, wherein the expressed bait polypeptide is whole *Saccharomyces cerevisiae* AGA1 or a functional fragment thereof, comprises a cell surface anchor, and is a membrane bound version.

Embodiment 4. The eukaryotic cell of a Cell Embodiment, wherein the cell surface anchor comprises a polypeptide segment sufficient to incorporate into membrane, trigger a covalent association with lipid (e.g., GPI), or associate with another membrane component. [Examples include without limitation functional segments of yeast *Saccharomyces* AGA1, CWP1 SED1 or GAS1 or mammalian GPI-anchored proteins such as cell surface receptors (e.g., folate receptor, CD14, and the like), cell adhesion molecules (such as segments of NCAM isoforms, carcinoembryonic antigen variants, fasciclin I, and the like having such adhesion), cell surface hydrolases (e.g. 5'-nucleotidase acetylcholinesterase, alkaline phosphatase, and the like), complement regulatory proteins (e.g., decay accelerating factor (CD55), and the like).]

Embodiment 5. The eukaryotic cell of a Cell Embodiment, wherein the bait polypeptide is a fragment of *Saccharomyces cerevisiae* AGA1 that lacks a cell surface anchor [e.g., glycosylphosphatidylinisotol membrane anchor] and is a soluble version.

Embodiment 6. The eukaryotic cell of a Cell Embodiment, wherein the prey polypeptide comprises *Saccharomyces cerevisiae* AGA2 or a functional fragment thereof, capable to form heterodimeric complex with the bait polypeptide.

Embodiment 7. The eukaryotic cell of a Cell Embodiment, wherein the scaffold protein comprises an immunoglobulin heavy chain variable region, a light chain variable region, combinations of light and heavy chain regions, Anticalins, fibronectin type III domain, Designed Ankyrin Repeat Protein or Centyrin.

Embodiment 8. The eukaryotic cell of a Cell Embodiment, wherein the expression of the membrane-bound version and the soluble version of a bait polypeptide are selectively inducible.

Embodiment 9. The eukaryotic cell of a Cell Embodiment, wherein the cell is a Saccharomyces cell or Pichia cell.

Embodiment 10. The eukaryotic cell of a Cell Embodiment, wherein the cell is a Chinese hamster ovary cell.

Embodiment 11. A method for maturing and identifying an antigen-binding variant of the scaffold protein comprising: A, cultivating a culture of eukaryotic cells of Embodiment 1; B. cultivating the culture such that the cytidine deaminase and the scaffold protein are expressed; C. contacting the culture with a mutagen; D. thereafter cultivating the culture such that the membrane-bound bait polypeptide and membrane bound said scaffold protein are expressed; E. selecting a subset of the eukaryotic cells that express scaffold protein at the cell surface that binds the antigen more strongly than the rest; F. cultivating the selected cells (e.g., colonies thereof) such that soluble bait polypeptide and soluble said scaffold protein are expressed; G. selecting a subset of one or more of the selected cells that bind the antigen (e.g., colonies), with selection based one or more of apparent binding activity, binding affinity or protein stability, for example based on the soluble scaffold protein.

Embodiment 12. The method of a Method Embodiment, wherein step D comprises contacting the culture with an inducer for the expression of the membrane-bound bait polypeptide.

Embodiment 13. The method of a Method Embodiment, wherein step F comprises contacting the culture with a second inducer, distinct from the first, which is for the expression of the soluble bait polypeptide.

Embodiment 14. The method of a Method Embodiment, wherein the cytidine deaminase is sea lamprey *Petromyzon marinus* cytidine deaminase CDA1 or functional fragment thereof.

Embodiment 15. The method of a Method Embodiment, wherein the expressed bait polypeptide is whole *Saccharomyces cerevisiae* AGA1 or a functional fragment thereof, comprises a cell surface anchor, and is a membrane bound version.

Embodiment 16. The method of a Method Embodiment, wherein the cell surface anchor comprises a polypeptide segment sufficient to incorporate into membrane, trigger a covalent association with lipid (e.g., GPI), or associate with another membrane component.

Embodiment 17. The method of a Method Embodiment, wherein the bait polypeptide lacks a cell surface anchor [e.g., glycosylphosphatidylinisotol membrane anchor] and is a soluble version.

Embodiment 18. The method of a Method Embodiment, wherein the prey polypeptide comprises *Saccharomyces cerevisiae* AGA2 or a functional fragment thereof capable to form heterodimeric complex with the bait.

Embodiment 19. The method of a Method Embodiment, wherein the scaffold protein comprises an immunoglobulin heavy chain variable region, a light chain variable region, combinations of light and heavy chain regions, Anticalins, fibronectin type III domain, Designed Ankyrin Repeat Protein or Centyrin.

Embodiment 20. The method of a Method Embodiment, wherein the expression of the membrane-bound version and the soluble version of a bait polypeptide are selectively inducible.

Embodiment 21. The method of a Method Embodiment, wherein the cell is a Saccharomyces cell or Pichia cell.

Embodiment 22. The method of a Method Embodiment, wherein the cell is a Chinese hamster ovary cell.

Publications and references, including but not limited to patents and patent applications, cited in this specification are herein incorporated by reference in their entirety in the entire portion cited as if each individual publication or reference were specifically and individually indicated to be incorporated by reference herein as being fully set forth. Any patent application to which this application claims priority is also incorporated by reference herein in the manner described above for publications and references.

The citations below are incorporated herein in there entirety, and particularly with respect to the subject matter for which they are cited.

Citations

BEERLI, R. R., M. BAUER, R. B. BUSER, M. GWERDER, S. MUNTWILER et al., 2008 Isolation of human monoclonal antibodies by mammalian cell display. Proc Natl Acad Sci USA 105: 14336-14341.

BODER, E. T., and K. D. WITTRUP, 1997 Yeast surface display for screening combinatorial polypeptide libraries. Nat Biotechnol 15: 553-557.

BODER, E. T., and K. D. WITTRUP, 2000 Yeast surface display for directed evolution of protein expression, affinity, and stability. Methods Enzymol 328: 430-444.

CHAO, G., W. L. LAU; B. J. HACKEL, S. L. SAZINSKY, S. M. LIPPOW et al., 2006 Isolating and engineering human antibodies using yeast surface display. Nat Protoc 1: 755-768.

CONRATH, K. E., M. LAUWEREYS, M. GALLENI, A. MATAGNE, J. M. FRERE et al., 2001 Beta-lactamase inhibitors derived from single-domain antibody fragments elicited in the camelidae, Antimicrob Agents Chemother 45: 2807-2812.

DE RUIJTER, J. C., E. V. KOSKELA and A. D. FREY, 2016 Enhancing antibody folding and secretion by tailoring the Saccharomyces cerevisiae endoplasmic reticulum. Microb Cell Fact 15: 87.

DRAKE, J. W., B. CHARLESWORTH, D. CHARLESWORTH and J. F. CROW, 1998 Rates of spontaneous mutation. Genetics 148: 1667-1686.

DUNCAN, B. K., and J. H. MILLER, 1980 Mutagenic deamination of cytosine residues in DNA. Nature 287: 560-561.

ECKER, D. M., S. D. JONES and H. L. LEVNE, 2015 The therapeutic monoclonal antibody market. MAbs 7: 9-14.

HANES, J., and A. PLUCKTHUN; 1997 In vitro selection and evolution of functional proteins by using ribosome display. Proc Natl Acad Sci USA 94: 4937-4942.

HAWKINS, R. E., S. J. RUSSELL and G. WINTER, 1992 Selection of phage antibodies by binding affinity. Mimicking affinity maturation. J Mol Biol 226: 889-896.

HE, M., and M. J. TAUSSIG, 1997 Antibody-ribosome-mRNA (ARM) complexes as efficient selection particles for in vitro display and evolution of antibody combining sites. Nucleic Acids Res 25: 5132-5134.

KIM, S. Y., J. H. SOHN, Y. R. PYUN and E. S. CHOI, 2002 A cell surface display system using novel GPI-anchored proteins in Hansenula polymorpha. Yeast 19: 1153-1163.

KJAERULFF, S., and M. R. JENSEN, 2005 Comparison of different signal peptides for secretion of heterologous proteins in fission yeast. Biochem Biophys Res Commun 336: 974-982.

KRAEBER-BODERE, F., C. BODET-MILIN, C. ROUSSEAU, T. EUGENE, A. PALLARDY et al., 2014 Radioimmunoconjugates for the treatment of cancer. Semin Oncol 41: 613-622.

LANG, G. I., and A. W. MURRAY, 2008 Estimating the per-base-pair mutation rate in the yeast Saccharomyces cerevisiae. Genetics 178: 67-82.

MAYOROV, V. I., I. B. ROGOZIN, L. R. ADKISON, C. FRAHM, T. A. KUNKEL et al., 2005a Expression of human AID in yeast induces mutations in context similar to the context of somatic hypermutation at G-C pairs in immunoglobulin genes. BMC Immunol 6: 10.

MAYOROV, V. I., I. B. ROGOZIN, L. R. ADKISON, C. FRAHM, T. A. KUNKEL et al., 2005b Expression of human AID in yeast induces mutations in context similar to the context of somatic hypermutation at G-C pairs in immunoglobulin genes. BMC Immunol 6: 10.

NOSKOV, V. N., K. STAAK, P. V. SHCHERBAKOVA, S. G. KOZMIN, K. NEGISHI et al., 1996 HAM1, the gene controlling 6-N-hydroxylaminopurine sensitivity and mutagenesis in the yeast Saccharomyces cerevisiae. Yeast 12: 17-29.

ORLEAN, P., and A. K. MENON, 2007 Thematic review series: lipid posttranslational modifications, GPI anchoring of protein in yeast and mammalian cells, or: how we learned to stop worrying and love glycophospholipids. J Lipid Res 48: 993-1011.

RAKESTRAW, J. A., D. AIRD, P. M. AHA, B. M. BAYNES and D. LIPOVSEK, 2011 Secretion-and-capture cell-surface display for selection of target-binding proteins. Protein Eng Des Sel 24: 525-530.

REIERSEN, H., I. LOBERSLI, G. A. LOSET, E. HVATTUM, B. SMONSEN et al., 2005 Covalent antibody display—an in vitro antibody-DNA library selection system. Nucleic Acids Res 33: e10.

RHIEL, L., S. KRAH, R. GUNTHER, S. BECKER, H. KOLMAR et al., 2014 REAL-Select: full-length antibody display and library screening by surface capture on yeast cells. PLoS One 9: el 14887.

ROGOZIN, I. B., L. M. IYER, L. LIANG, G. V. GLAZKO, V. G. LISTON et al., 2007 Evolution and diversification of lamprey antigen receptors: evidence for involvement of an AID-APOBEC family cytosine deaminase, Nat Immunol 8: 647-656.

SHAHEEN, H. H., B. PRINZ, M. T. CHEN, T. PAVOOR, S. LIN et al., 2013 A dual-mode surface display system for the maturation and production of monoclonal antibodies in glycoengineered Pichia pastoris. PLoS One 8: e70190.

SHCHERBAKOVA, P. V., and Y. I. PAVLOV, 1993 Mutagenic specificity of the base analog 6-N-hydroxylaminopurine in the URA3 gene of the yeast Saccharomyces cerevisiae. Mutagenesis 8: 417-421.

SHEN, Z. M., L. WANG, J. PIKE, C. K. JUE, H. ZHAO et al., 2001 Delineation of functional regions within the subunits of the Saccharomyces cerevisiae cell adhesion molecule a-agglutinin. J Bial Chem 276: 15768-15775.

SIKORSKI, R. S., and P. HIETER, 1989 A system of shuttle vectors and yeast host strains designed for efficient manipulation of DNA in Saccharomyces cerevisiae. Genetics 122: 19-27.

STUDIER, F. W., 2005 Protein production by auto-induction in high density shaking cultures. Protein Expr Purif 41: 207-234.

VU, K. B., M. A. GHAHROUDI, L. WYNS and S. MUYLDERMANS, 1997 Comparison of llama VH sequences from conventional and heavy chain antibodies. Mol Immunol 34: 1121-1131.

What is claimed is:

1. A eukaryotic cell providing a protein display, protein selection and soluble protein recovery system, comprising:
   a) recombinant DNA capable of expressing a mutagenic cytidine deaminase;
   b) recombinant DNA capable of expressing a membrane-bound version of a bait polypeptide;
   c) recombinant DNA capable of expressing a soluble version of the bait polypeptide; and
   d) recombinant DNA capable of expressing one or more polypeptides of a scaffold protein, with one or more said scaffold polypeptides operably fused to a prey polypeptide.

2. The eukaryotic cell of claim 1, wherein the cytidine deaminase is sea lamprey *Petromyzon marinus* cytidine deaminase CDA1 or functional fragment thereof.

3. The eukaryotic cell of claim 1, wherein the expressed bait polypeptide is whole *Saccharomyces cerevisiae* AGA1 or a functional fragment thereof, comprises a cell surface anchor, and is a membrane bound version.

4. The eukaryotic cell of claim 3, wherein the cell surface anchor comprises a polypeptide segment sufficient to incorporate into membrane, trigger a covalent association with lipid, or associate with another membrane component.

5. The eukaryotic cell of claim 1, wherein the bait polypeptide is a fragment of *Saccharomyces cerevisiae* AGA1 that lacks a cell surface anchor and is a soluble version.

6. The eukaryotic cell of claim 1, wherein the prey polypeptide comprises *Saccharomyces cerevisiae* AGA2 or a functional fragment thereof, capable to form heterodimeric complex with the bait.

7. The eukaryotic cell of claim 1, wherein the scaffold protein comprises an immunoglobulin heavy chain variable region, a light chain variable region, combinations of light and heavy chain regions, Anticalins, fibronectin type Ill domain, Designed Ankyrin Repeat Protein or Centyrin.

8. The eukaryotic cell of claim 1, wherein the expression of the membrane-bound version and the soluble version of a bait polypeptide are selectively inducible.

9. The eukaryotic cell of claim 1, wherein the cell is a Saccharomyces cell or Pichia cell.

10. The eukaryotic cell of claim 1, wherein the cell is a Chinese hamster ovary cell.

11. A method for maturing and identifying an antigen-binding variant of the scaffold protein comprising
    A. cultivating a culture of eukaryotic cells of claim 1;
    B. cultivating the culture such that the cytidine deaminase and the scaffold protein are expressed;
    C. contacting the culture with a mutagen;
    D. thereafter cultivating the culture such that the membrane-bound bait polypeptide and the scaffold protein are expressed;
    E. selecting a subset of the eukaryotic cells that express scaffold protein at the cell surface that binds the antigen more strongly than the rest;
    F. cultivating colonies of the selected cells such that soluble bait polypeptide and the scaffold protein are expressed;
    G. selecting a subset of one or more of the colonies that bind the antigen, with selection based one or more of apparent binding activity, binding affinity or protein stability.

12. The method of claim 11, wherein step D comprises contacting the culture with an inducer for the expression of the membrane-bound bait polypeptide.

13. The method of claim 12, wherein step F comprises contacting the culture with a second inducer, distinct from the first, which is for the expression of the soluble bait polypeptide.

14. The method of claim 11, wherein the cytidine deaminase is sea lamprey *Petromyzon marinas* cytidine deaminase CDA1 or functional fragment thereof.

15. The method of claim 11, wherein the expressed bait polypeptide is whole *Saccharomyces cerevisiae* AGA1 or a functional fragment thereof, comprises a cell surface anchor, and is a membrane bound version.

16. The method of claim 15, wherein the cell surface anchor comprises a polypeptide segment sufficient to incorporate into membrane, trigger a covalent association with lipid (e.g., GPI), or associate with another membrane component.

17. The method of claim 15, wherein the bait polypeptide is a fragment of *Saccharomyces cerevisiae* AGA1 that lacks a cell surface anchor and is a soluble version.

18. The method of claim 15, wherein the prey polypeptide comprises *Saccharomyces cerevisiae* AGA2 or a functional fragment thereof capable to form heterodimeric complex with the bait.

19. The method of claim 11, wherein the scaffold protein comprises an immunoglobulin heavy chain variable region, a light chain variable region, combinations of light and heavy chain regions, Anticalins, fibronectin type Ill domain, Designed Ankyrin Repeat Protein or Centyrin.

20. The method of claim 11, wherein the cell is a Saccharomyces cell or Pichia cell.

21. The method of claim 11, wherein the cell is a Chinese hamster ovary cell.

* * * * *